(12) United States Patent
Kim et al.

(10) Patent No.: US 8,394,845 B2
(45) Date of Patent: *Mar. 12, 2013

(54) METHOD OF USING COMBINATION PREPARATION COMPRISING ANGIOTENSIN-II-RECEPTOR BLOCKER AND HMG-COA REDUCTASE INHIBITOR

(75) Inventors: Sung Wuk Kim, Seongnam (KR); Sung Soo Jun, Seongnam (KR); Young Gwan Jo, Daejeon (KR); Ja Seong Koo, Daejeon (KR); Jae Woon Son, Suwon (KR)

(73) Assignee: Hanall Biopharma Co., Ltd., Daejeon (KR)

( * ) Notice: Subject to any disclaimer, the term of this patent is extended or adjusted under 35 U.S.C. 154(b) by 0 days.

This patent is subject to a terminal disclaimer.

(21) Appl. No.: 13/105,791

(22) Filed: May 11, 2011

(65) Prior Publication Data

US 2011/0213004 A1 Sep. 1, 2011

Related U.S. Application Data

(63) Continuation-in-part of application No. 12/513,054, filed as application No. PCT/KR2007/005405 on Oct. 30, 2007.

(30) Foreign Application Priority Data

Oct. 30, 2006 (KR) .................. 10-2006-0105617

(51) Int. Cl.
*A01N 43/64* (2006.01)
(52) U.S. Cl. ..................................... 514/381
(58) Field of Classification Search .................. 514/381
See application file for complete search history.

(56) References Cited

U.S. PATENT DOCUMENTS

| 5,138,069 A | 8/1992 | Carini et al. |
| 6,228,398 B1 * | 5/2001 | Devane et al. ............ 424/484 |
| 2007/0254932 A1 * | 11/2007 | Tomiyama et al. ........... 514/381 |
| 2008/0096866 A1 | 4/2008 | Woo et al. |

FOREIGN PATENT DOCUMENTS

| KR | 10-0582347 B1 | 5/2006 |
| WO | 9933448 A1 | 7/1999 |
| WO | 0115674 A1 | 3/2001 |
| WO | 03020243 A1 | 3/2003 |
| WO | 2005009413 A1 | 2/2005 |
| WO | WO2006/001090 | * 1/2006 |

OTHER PUBLICATIONS

Sheng-Fang Su, et al, Effects of Pravastatin on Left Ventricular Mass in Patients With Hyperlipidemia and Essential Hypertension, 86 Am. J Cardiol. 514 (2000).*
G.R. Thompson, F. O'Neill & M. Seed, Why Some Patients Respond Poorly to Statins and How This Might be Remedied, 23 Eur. Heart J 200 (2002).*

P. Wilson, et al.: "Coronary Risk Prediction in Adults (The Framingham Heart Study)," Am. J. Cardiol. vol. 59, pp. 91G-94G, 1987.
J. Wagner, et al.: "Effects of AT1 Receptor Blockade on Blood Pressure and the Renin-Angiotensin System in Spontaneously Hypertensive Rats of the Stroke Prone Strain," Clin. Exper. Hypertens., vol. 20, No. 2, pp. 205-221, 1998.
M. Böhm, et al.: "Angiotensin II receptor blockade in TGR(mREN2)27: effects of renin-angiotensin-system gene expression and cardiovascular functions," J. Hypertens., vol. 13, No. 8, pp. 891-899, 1995.
S. Andersen, et al.: "Renoprotective effects of angiotensin II receptor blockade in type 1 diabetic patients with diabetic nephropathy," Kid. Internat., vol. 57, pp. 601-606, 2000.
L. Ruilope: "Renoprotection and Renin-Angiotensin System Blockade in Diabetes Mellitus," Am. J. Hypertens., vol. 10, No. 12, pp. 325S-331S, Dec. 1997.
E. Schiffrin, et al.: "Correction of Arterial Structure and Endothelial Dysfunction in Human Essential Hypertension by the Angiotensin Receptor Antagonist Losartan," Circulation, vol. 101, pp. 1653-1659, Apr. 11, 2000.
R. Touyz, et al.: "Angiotensin II stimulates DNA and protein synthesis in vascular smooth muscle cells from human arteries: role of extracellular signal-regulated kinases," J. Hypertens., vol. 17, No. 7, pp. 907-916, 1999.
A. Prasad, et al.: "Acute and Chronic Angiotensin-1 Receptor Antagonism Reverses Endothelial Dysfunction in Atherosclerosis," Circulation, vol. 101, pp. 2349-2354, May 23, 2000.
E. Schiffrin: "Vascular Remodeling and Endothelial Function in Hypertensive Patients: Effects of Antihypertensive Therapy," Scand. Cardiovasc. J. Suppl., vol. 32, supp. 47, pp. 15-21, 1998.
T. Pedersen et al.: "Randomised trial of cholesterol lowering in 4444 patients with coronary heart disease" The Lancet, vol. 344, pp. 1383-1389, Nov. 19, 1994.
K. Gould, et al.: "Non-invasive management of coronary artery disease," The Lancet, vol. 346, pp. 750-753, Sep. 16, 1995.
J. Shepherd: "Preventing Coronary Artery Disease in the West of Scotland: Implications for Primary Prevention," Am. J. Cardiol., vol. 82, No. 10B, pp. 57T-59T, Nov. 26, 1998.
A. Tonkin, et al.: "Management of the Long-term Intervention with Pravastatin in Ischaemic Disease (LIPID) Study after the scandinavian Simvastatin Survival Study (4S)," Am. J. Cardiol., vol. 76, pp. 107C-112C, Sep. 28, 1995.

(Continued)

*Primary Examiner* — Sean Basquill
(74) *Attorney, Agent, or Firm* — Edwards Wildman Palmer LLP

(57) ABSTRACT

Disclosed herein is a combination therapy and a combination preparation of an angiotensin-II-receptor blocker and an HMG-CoA reductase inhibitor characterized in that the angiotensin-II-receptor blocker is absorbed substantially later than the HMG-CoA reductase inhibitor. As the angiotensin-II-receptor blocker and the HMG-CoA reductase inhibitor are released at different times, the present combination therapy prevents competitive inhibition between the two drugs and side effects, as well as simultaneously provides synergistic effects for each active ingredient and convenience of taking the drugs.

10 Claims, 11 Drawing Sheets

OTHER PUBLICATIONS

K. Matsubara, et al.: "Current Status of Lipid Management of Hypertensive Patients," Hypertens. Res., vol. 26, No. 9, pp. 699-704, 2003.

M. Minami, et al.: "Effects of Cholesterol-Lowering Therapy on Pressor Hyperreactivity to Stress in Hypercholesterolemic Patients," Hypertens. Res., vol. 26, No. 4, pp. 273-280, 2003.

D. Wood: "Asymptomatic individuals—risk stratification in the prevention of coronary heart disease," Br. Med. Bull., vol. 59, pp. 3-16, 2001.

A. Gotto: "Risk Factor Modification: Rationale for Management of Dyslipidemia," Am. J. Med., vol. 104, No. 2A, pp. 6S-8S, 1998.

D. Williams, et al.: "Pharmacokinetic-Pharmacodynamic Drug Interactions with HMG-CoA Reductase Inhibitors," Clin. Pharmacokinet., vol. 41, No. 5, pp. 343-370, 2002.

S. Vickers, et al.: "Metabolic Disposition Studies on Simvastatin, A Cholesterol-Lowering Prodrug," Drug Metab. Dispos., vol. 18, No. 2, pp. 138-145, 1990.

S. Vickers, et al. "In Vitro and In Vivo Biotransformation of Simvastatin, an Inhibitor of HMG CoA Reductase," Drug Metab. Dispos., vol. 18, No. 4, pp. 476-483, 1990.

T. Prueksaritanont, et al.: "In Vitro Metabolism of Simvastatin in Humans [SBT]Identification of Metabolizing Enzymes and Effect of the Drug on Hepatic P450S," Drug Metab. & Dispos., vol. 25, No. 10, pp. 1191-1199, 1997.

P. Neuvonen, et al.: "Simvastatin but not pravastatin is very susceptible to interaction with the CYP3A4 inhibitor Itraconazole," Clin. Pharm. & Ther., vol. 63, No. 3, pp. 332-341, 1998.

T. Kantola, et al.: "Erythromycin and verapamil considerably increase serum simvastatin and simvastatin acid concentrations," Clin. Pharm. Ther., vol. 64, No. 2, pp. 177-182, 1998.

Physicians Desk Reference, "Zocor," 19 pages, 2006.

D. Sutton, et al.: "Role of CYP3A4 in Human Hepatic Diltiazem N-Demethylation: Inhibition of CYP3A4 Activity by Oxidized Diltiazem Metabolites," J. Pharmacol. Exp. Ther., vol. 282, No. 1, pp. 294-300, 1997.

D. Jones, et al.: "Diltiazem Inhibition of Cytochrom P-450 3A Activity is Due to Metabolite Intermediate Complex Formation," J. Pharmacol. Exp. Ther., vol. 290, No. 3, pp. 1116-1125, 1999.

H. Watanabe, et al.: "Pharmacokinetic and pharmacodynamic interactions between simvastatin and diltiazem in patients with hypercholesterolemia and hypertension," Life Sci., vol. 76, pp. 281-292, 2004.

Y. Saito, et al.: "Comparison between morning and evening doses of simvastatin in hyperlipidemic subjects. A double-blind comparative study," Arterioscler. Thromb., vol. 11, No. 4, pp. 816-826, 1991.

D. Illingworth: "Comparative efficacy of once versus twice daily mevinolin in the therapy of familiar hypercholesterolemla," Clin. Pharmacol. Ther., vol. 40, No. 3, pp. 338-343, 1986.

Dept. of Medicine, Indiana University: "Cytochrome P450 Drug Interaction Table," http://medicine.iupui.edu/flockhart/table.htm, 2 pages, updated Mar. 11, 2004.

* cited by examiner

METHOD OF USING COMBINATION PREPARATION COMPRISING ANGIOTENSIN-II-RECEPTOR BLOCKER AND HMG-COA REDUCTASE INHIBITOR

CROSS-REFERENCE TO RELATED APPLICATIONS

The present application is a continuation in part of application U.S. application Ser. No. 12/513,054 filed Jul. 10, 2009, which is a 371 national phase of PCT/KR07/005,405 filed Oct. 30, 2007, which claims priority to KR Patent application No. 10-2006-0105617 filed Oct. 30, 2006, the entire contents of which applications are incorporated herein by reference.

TECHNICAL FIELD

The present invention relates to a combination therapy of an angiotensin-II-receptor blocker and an HMG-CoA reductase inhibitor, whose design is based on xenobiotics and chronotherapy. Xenobiotics is the study of metabolism and interactions of substances (for example, drugs) which are found in an organism but are not normally produced or expected to be present. Chronotherapy is the study of timing drug administration for reducing side effects and inducing ideal effects considering the biorhythms of diseases. Specifically, the present invention relates to a method of preventing or treating hypertension, hyperlipidemia, cardiovascular diseases, cardiopulmonary diseases, pulmonary diseases, renal disorders, or metabolic syndromes, which comprises administrating a therapeutically effective amount of an angiotensin-II-receptor blocker and an HMG-CoA reductase inhibitor to a subject such that the drugs can be absorbed at different times, thereby showing the ideal effectiveness of the drugs, and a combination preparation for use in the method, which are designed in consideration of in-vivo metabolism and drug interactions of an angiotensin-II-receptor blocker and an HMG-CoA reductase inhibitor, as well as the biorhythms of diseases.

BACKGROUND OF THE INVENTION

Necessity of the Combination Therapy

Hypertension frequently coexists with coronary artery disease and both are considered to be major risk factors for developing cardiac disease. This clustering of risk factors is potentially due to a common mechanism. Arteriosclerosis, aggravated by hypertension and hyperlipidemia, is a condition which becomes worse when both symptoms coexist. When blood pressure increases, arteriosclerosis becomes worse, and when arteriosclerosis becomes worse, blood pressure increases to worsen arteriosclerosis. Also, these conditions are considered to be severe risk factors for developing cardiovascular diseases. For example, hypercholesterolemia and hyperlipidemia are involved in the early development of atherosclerosis, which is characterized in that lipid deposits are uniformly deposited inside artery including the coronary artery, carotid artery and peripheral artery. Accordingly, this irregular lipid deposition is characteristic of coronary heart damage and cardiovascular diseases, the gravity and prevalence of which are also affected by the existence of diabetes, the sex of the person, smoking, and left ventricular hypertrophy occurring as a side effect of hypertension [see Wilson et al., Am. J. Cardiol., vol. 59(14)(1987), p. 91G-94G]. Thus, it is already well known that it would be beneficial for patients to receive combination therapy in order to treat such conditions.

It is already well known that the application and administration of an HMG-CoA reductase inhibitor in formulation with an angiotensin-II-receptor blocker are beneficial for the treatment of cardiovascular diseases and renal diseases. However, there is no report relating to combination therapies in which the drugs can be absorbed at different times considering pharmacological mechanisms including absorption, distribution and metabolism or the biorhythms of diseases, or a combination preparation whose releasing can be controlled for use in such combination therapies.

Information on Active Pharmaceutical Ingredients

Losartan, which is a typical agent among angiotensin-II-receptor blockers, and simvastatin, which is a typical agent among HMG-CoA reductase inhibitors, are the most frequently used in combination therapies. The combination application of components contained in the combination therapy of the present invention is reasonable, and the pharmacological effect of each component is ideal as shown in Table 1 below.

TABLE 1

| | | Losartan | Simvastatin |
|---|---|---|---|
| 1) | Blood pressure reducing | By suppressing RAAS[1] and vasodilation | By preventing atherosclerosis and vasodilation |
| | | Combination therapy of the two components increases the antihypertensive effect of losartan and increases the lipid-reducing effect of simvastatin. | |
| 2) | Chronotherapy | Excellent antihypertensive action after midnight while RAAS is active. | Pharmacological action is exhibited in the evening while lipid synthesis is most active. |
| | | When the combination of the two components is administered at about 7 p.m., the optimal antihypertensive effect is maintained at the time the risk of developing complications is high, after patients showing signs of non-dipper hypertension[2] rise in the morning. | |
| 3) | Atherosclerosis | | Substantial lipid-reducing action |
| 4) | Change of vascular walls | (1) Inhibiting the proliferation of disease cells in vascular walls. (2) Regenerating endothelial cells and maintaining the function of the cells. | (1) anti-inflammatory action (2) cell-regeneration |
| | | The administration of the two components enhances and maintains the function of endothelial cells. | |

TABLE 1-continued

| | Losartan | Simvastatin |
|---|---|---|
| 5) glomerular artery | Relaxing efferent artery | Inhibiting sclerosis of afferent and efferent arteries |
| | The combination administration of the two components enhances renal function | |
| 6) Vasodilation | Vasodilation | Vasodilation |
| | The combination administration of the two components further vasodilates blood vessels | |
| 7) Inflammatory factors MDA-CRP MCP-1 | Reducing | Reducing |
| | The combination administration of the two components further reduces inflammation-causing substances | |
| 8) Insulin activity | Increasing | Increasing, Increasing adiponectin |
| | The administration of the two components increases insulin sensitivity | |

[1] RAAS (Renin and Angiotensin System): one of the body's blood pressure regulatory mechanisms
[2] non-dipper hypertensive patients: their blood pressure is not reduced in their sleep, unlike general hypertensive patients, and have a higher risk of complications such as stroke; mostly found in the elderly, diabetic patients, cardiac hypertrophy patients etc.

1) Losartan as an Angiotensin-II-Receptor Blocker and Pharmaceutical Use Thereof Losartan, having the chemical name of 2-butyl-4-chloro-1-[2-(1H-tetrazol-5-yl)biphenyl-4-ylmethyl]-1H-imidazole-5-methanol, is an antihypertensive agent which antagonizes the binding of angiotensin-II (AII) to a vascular receptor (AII receptor). The angiotensin II is a factor, which increases blood pressure and causes left ventricular hypertrophy, vascular hypertrophy, atherosclerosis, renal failure, stroke and the alike (see U.S. Pat. No. 5,138,069).

The angiotensin-II-receptor blocker is a drug which acts to reduce blood pressure and, at the same time, shows a wide range of effects including the prevention and treatment of renal failure, the prevention and treatment of myocardial infarction arrhythmia and heart failure, the prevention and treatment of diabetic complications, the prevention and treatment of stroke, antiplatelet effects, the prevention of atherosclerosis, the inhibition of harmful aldosterone effects, the reduction of metabolic syndrome effects, and the effect of preventing cardiovascular diseases from growing worse in a chain manner [see Clin, Exp. Hypertens., vol. 20 (1998), [p. 205-221]; J. Hypertens, vol. 13 (8) (1995), [p. 891-899]; Kidney Int., vol. 57(2)(2000), [p. 601-606]; Am. J. Hypertens., vol. 10 (12PT2) Suppl. (1997), [p. 325-331]; Circulation, vol. 101(14)(2000), [p. 1653-1659]; J. Hypertension., vol 17 (7) (1999), [p. 907-716]; Circulation, vol. 101 (2000), p. 2349].

The antihypertensive and renal protective effects of angiotensin-II-receptor blockers including losartan, are described in, for example, the following publications: J. Wagner et al., Effects of AT1 receptor blockade on blood pressure and the renin angiotensin system in spontaneously hypertensive rats of the stroke prone strain, Clin, Exp. Hypertens., vol. 20 (1998), p. 205-221; M. Bohm et al., angiotensin-II-receptor blockade in TGR(mREN2)27: Effects of renin-angiotensin-system gene expression and cardiovascular functions, J. Hypertens., vol. 13(8)(1995), p. 891-899.

Other renal protective effects of angiotensin-II-receptor blockers, found in the first clinical trials, are described in the following publications: S. Andersen et al., Renoprotective effects of angiotensin-II-receptor blockade in type 1 diabetic patients with diabetic nephropathy, Kidney Int., vol. 57(2) (2000), p. 601-606; L. M. Ruilope, Renoprotection and renin-angiotensin system blockade in diabetes mellitus, Am. J. Hypertens., vol. 10 (12PT2) Suppl. (1997), p. 325-331.

The effects of angiotensin-II-receptor blockers on endothelial dysfunction are described in the following publications: E. L. Schiffrin et al., Correction of arterial structure and endothelial dysfunction in human essential hypertension by the angiotensin receptor antagonist losartan, Circulation, vol. 101(14)(2000), p. 1653-1659; R. M. Touyz et al., Angiotensin-II-stimulates DNA and protein synthesis in vascular smooth muscle cells from human arteries: role of extracellular signal-regulated kinases, J. Hypertension., vol 17 (7) (1999), p. 907-'716; E. L Schiffrin, Vascular remodeling and endothelial function in hypertensive patients: Effect of antihypertensive therapy, Scand. Cardiovasc. J., vol. 32, Suppl. 47 (1998) p. 15-21; Prasad, Acute and Chronic angiotensin-1 receptor reverses endothelial dysfunction in atherosclerosis, Circulation, vol. 101 (2000), p. 2349.

Also, it is known that angiotensin-II-receptor blockers block AT1 receptors, but do not affect AT2 receptors, which inhibit growth and tissue regeneration.

2) Simvastatin as HMG-CoA reductase inhibitor and pharmaceutical use thereof Simvastatin is a typical statin-based lipid-reducing agent, which is the most frequently used HMG-CoA reductase inhibitor.

Simvastatin serves to strongly inhibit HMG-CoA reductase which converts 3-hydroxy-3-methylglutaryl-coenzyme A (HMG-CoA) into mevalonate, thus showing the effects of inhibiting the production of cholesterol in the liver and reducing low-density lipoprotein cholesterol (LDL-C) levels. Due to such effects, simvastatin is excellent in treating composite hyperlipidemia, as well as treating and preventing atherosclerosis. Furthermore, it was proven through studies that the effect of reducing low-density lipoprotein cholesterol levels is highly effective against coronary heart diseases [see "Scandinavian Simvastatin Survival Study" published in the Lancet, vol. 344, (1994), p. 1383-89].

It is known that a statin-based lipid-reducing agent as an HMG-CoA reductase inhibitor is a primary drug for the prevention and treatment of heart diseases resulting from coronary artery atherosclerosis including angina or myocardial infarction [see Lancet 1995; 346: 750-753, Am J Cardiol 1998; 82: 57T-59T, Am J Cardiol 1995; 76: 107C-112C, Hypertens Res 2003; 26: 699-704, Hypertens Res 2003; 26: 273-280.] Br Med Bull 2001; 59: 3-16, Am J Med 1998; 104 (Suppl 1): 6S-8S, Clin Pharmacokinet 2002; 41: 343-370].

Also, among HMG-CoA reductase inhibitors, simvastatin is most frequently used, and the efficacy in the treatment of coronary heart diseases and a reduction in the mortality rate of these diseases have been proven through large-scale clinical trials [see Lancet 1994; 344: 1383-1389].

This effect is due to simvastatin's strong inhibition of HMG-CoA reductase's ability to synthesize cholesterol in the liver and, at the same time, inhibits inflammation-causing factors [see "Scandinavian Simvastatin Survival Study" published in the Lancet, 1994, 344, 1383-89].

Simvastatin is a lactone-based compound, which is inactive by itself. Simvastatin primarily enters the liver, where it changes into its active form, β-hydroxyacid, displaying lipid-reducing action. The remaining simvastatin is also metabolized in several steps by cytochrome P450 3A4 in the liver, and some of the metabolites exhibit a potent lipid-reducing effect.

Simvastatin and its β-hydroxyacid are metabolized by enzyme cytochrome P450 3A4 in the liver, and they are acting in the liver while they are partially released into the blood vessel [see Drug Metab Dispos 1990; 18: 138-145, Drug Metab Dispos 1990; 18: 476-483, Drug Metab Dispos 1997; 25: 1191-1199].

As the synthesis of lipid in the liver becomes active after dinner in the early evening, it is recommended that statins be administered in the early evening [see Arterioscler Thromb 11: 816-826, Clinic Pharmacol Ther 40: 338-343].

3) Atorvastatin as a HMG-CoA Reductase Inhibitor and Pharmaceutical Use Thereof

As with most prescription HMG-CoA reductase inhibitors, atorvastatin strongly inhibits the reduction of 3-hydroxy-3-methylglutaryl-coenzyme A (HMG-CoA) to mevalonate by HMG-CoA reductase, thus blocking hepatic cholesterol biosynthesis and decreasing the amount of LDL-cholesterol in the blood. Thus, atorvastain shows excellent effects in the treatment of combined hyperlipidemia and the treatment of arteriosclerosis in otherwise clinically normal patients and the prevention of its progression. Furthermore, atorvastatin is very effective in treating cardiovascular disease since it can decrease the amount of LDL-cholesterol.

Problem of Simple Combination Therapy

It is already well known that the application and administration of an angiotensin-II-receptor blocker together with an HMG-CoA reductase inhibitor are advantageous for the treatment of cardiovascular diseases and renal diseases. However, when an HMG-CoA reductase inhibitor such as simvastatin is used together with a drug, which is metabolized by cytochrome P450 3A4 enzyme, the metabolism of simvastatin in the liver will be inhibited, so that the blood level of simvastatin will be increased. For this reason, serious side effects such as myolysis can occur [see Clin Pharmacol Ther 1998; 63: 332-341; Clin Pharmacol Ther 1998; 64: 177-182; Physicians' Desk Reference 2006 (Zocor); J Pharmacol Exp Ther 1997; 282: 294-300; Pharmacol Exp Ther 1999; 290: 1116-1125; Life Sci 2004; 76: 281-292].

If the administration of two drug does create more risk than benefit, the combination administration should be avoided in principle. However, an angiotensin-II-receptor blocker and an HMG-CoA reductase inhibitor, particularly losartan and simvastatin, have been prescribed together despite the risk of side effects, such as myopathy, to be likely caused by the inhibitory effect of losartan against simvastatin through completive inhibition on the same cytochrome P450 3A4 enzyme. The co-administration of the two drugs shows remarkable synergistic effects.

Simvastatin strongly inhibits the conversion activity of HMG-CoA reductase 3-hydroxy-3-methylglutaryl-coenzyme A (HMG-CoA) to mevalonate, thus showing the effects of inhibiting the production of cholesterol in the liver and reducing low-density lipoprotein cholesterol (LDL-C) levels.

For this, lipid-reducing effect, simvastatin should act in the liver. Meanwhile, simvastatin is a first-pass drug which is absorbed from the small intestines upon administration and enters the liver. It is mostly changed into an active type by cytochrome P450 3A4 in the liver, and then acts in the liver, and is metabolized in the liver, and excreted from the liver. The remaining simvastatin, not metabolized by cytochrome P450 3A4, moves into the blood stream to reach the whole body, and accounts for about 5% of the administered simvastatin. An increase in levels of simvastatin in the blood has no connection with the therapeutic effect of inhibiting the production of cholesterol, but rather that the risk of causing myopathies, such as myolysis, which is the side effect of simvastatin, is further increased.

Losartan, after absorbed from the small intestines, enters the liver. A portion thereof is released into the blood stream in the form of an active losartan molecule, which then reaches the mean peak concentration in the blood within 1 hour. However, the remaining portion is metabolized by two enzymes, cytochrome P450 2C9 and 3A4, in the liver, so as to be changed into losartan carboxylic acid (losartan's active metabolite) having higher activity, later reaching its highest concentration in blood after 3-4 hours. That is, the pharmacological action of losartan is the pharmacological action of a mixture of losartan with losartan carboxylic acid (losartan's active metabolite). About 14% of the orally-administered dose of losartan is converted into the form of losartan carboxylic acid (active metabolite) by enzymes in the liver, and the active metabolite exhibits pharmacological activity more 40 times than that of losartan. The blood excretion rate is 600 mL/min for losartan and 50 mL/min for losartan carboxylic acid (active metabolite), suggesting that the active metabolite shows a slower excretion rate, and thus plays an important role in maintaining the long-lasting action time.

Also, most of angiotensin-II-receptor blockers and HMG-CoA reductase inhibitors are substrates of P-Glycoprotein transporter. That is, when both angiotensin-II-receptor blocker and HMG-CoA reductase inhibitor are absorbed in gastrointestinal tract, bioavailability of the drugs may be affected due to drug interactions between the two drugs. For example, losartan that is angiotensin-II-receptor blocker and atorvastin that is HMG-CoA reductase inhibitor are substrates of P-Glycoprotein transporter. Pailwal et al have reported that both losartan and atorvastin are substrates of P-Glycoprotein transporter, thus bioavailability of the drugs can be influenced by their drug interaction.

From this point of view, when an HMG-CoA reductase inhibitor such as simvastatin/atorvastatin and an angiotensin-II-receptor blocker such as losartan are administered simultaneously, the following problems will occur.

If simvastatin/artorvastatin and losartan simultaneously enter the liver, due to the competitive inhibition between the two drugs in the liver, thus the portion of simvastatin will not be metabolized by cytochrome P450, and released into blood, resulting in a reduction in the effect of HMG-CoA reductase inhibition and increasing the risk of side effects. Meanwhile, the conversion of losartan to losartan carboxylic acid (active metabolite) will be inhibited and the effect of losartan will be reduced. In addition, simvastatin/artorvastatin and losartan competitively bind to P-glycoprotein efflux transporter, thus the risk of side effects can be increased due to rising drug concentrations in the blood. Therefore, if the two drugs are simultaneously co-administered, they cannot show the optimal effect according to combination therapy because they antagonize each other

Examples of Prior Art

As combination therapies for improving various disease conditions, combination therapies of HMG-CoA reductase inhibitors and angiotensin-II-receptor blockers have been suggested as follows.

International Patent Publication No. WO 95/26188 discloses a method of treatment for atherosclerosis and reducing cholesterol using an HMG-CoA reductase inhibitor and an angiotensin-II-receptor blocker. Losartan is described to be a usable angiotensin-II-receptor blocker.

International Patent Publication No. WO 97/37688 discloses a combination therapy of an HMG-CoA reductase inhibitor and an angiotensin-II-receptor blocker for treating many symptoms including hypertension and atherosclerosis.

International Patent Publication No. WO 99/11260 discloses a combination use of atorvastatin, losartan, irbesartan and valsartan for reducing blood pressure and lipid levels and treating angina and atherosclerosis in mammals.

International Patent Publication No. WO 00/45818 discloses a combination use of an HMG-CoA reductase inhibitor and an angiotensin-II-receptor blocker for improving diabetic neuropathy, specifically improving nerve conduction velocity and nerve blood flow in patients suffering from diabetes.

International Patent Publication No. WO 04/062729 discloses a combination therapy of simvastatin as an HMG-CoA reductase inhibitor, and telmisartan as an angiotensin-II-receptor blocker for the prevention or treatment of cardiovascular, cardiopulmonary, pulmonary or renal diseases.

International Patent Publication No. WO 06/040085 discloses a bilayered tablet for the prevention or treatment of cardiovascular, cardiopulmonary, pulmonary or renal diseases, which comprises simvastatin as an HMG-CoA reductase inhibitor, and telmisartan as an angiotensin-II-receptor blocker. The disclosed bilayered tablet is a combination in which simvastatin and telmisartan are simultaneously released. In terms of a logical or pharmacological point of view, this kind of combination therapy is thought to be inappropriate for obtaining the optimal synergistic effects of the two drugs. This kind of therapy, when the HMG-CoA reductase inhibitor and the angiotensin-II-receptor blocker are simultaneously introduced into the liver, the metabolisms thereof by cytochrome P450 3A4 will be competitive, and thus the HMG-CoA reductase inhibitor will be released into blood without being metabolized in the liver. That is, the above said patent publications have problems in that the HMG-CoA reductase inhibitor, which should be metabolized in the liver to act in the liver, shall be released into blood without being sufficiently metabolized, resulting in the unnecessary high increase of the blood level of the simvastatin and its metabolites, which may lead to myopathy.

Such a simple combination product may well not be patentable due to lack of any inventiveness. Korean Patent Publication No. 2000-7002144 was rejected, because it relates to a simple combination.

SUMMARY OF THE INVENTION

If a HMG-CoA reductase inhibitor such as simvastatin/ artorvastatin and an angiotensin-II-receptor blocker such as losartan simultaneously enter the liver, due to the competitive inhibition between the two drugs in the liver, the portion of HMG-CoA reductase inhibitor would not be metabolized by cytochrome P450 and would be released into blood. This will result in reducing the effect of the HMG-CoA reductase inhibition and increasing the risk of side effects. Meanwhile, the conversion of losartan to losartan carboxylic acid (active metabolite) will be inhibited and the effect of losartan will be reduced. Furthermore, simvastatin/artorvastatin and losartan are competitive substrates to P-glycoprotein efflux transporter, thus the risk of side effects is elevated due to rising drug concentrations in the blood. Therefore, if the two drugs are simultaneously co-administered, they cannot show optimal effect as a combination therapy because they antagonize each other.

Accordingly, the present inventors have developed a novel combination therapy of an angiotensin-II-receptor blocker and HMG-CoA reductase inhibitor for the first time in the world, in which the combination therapy reduces side effects, such as myolysis, occurring if the two drugs are simultaneously co-administered, and in which two active pharmaceutical ingredients, from a pharmacological viewpoint, will fully carry out their expected pharmacological effects through sufficient metabolism, and will provide clinical synergistic effects each are released at a desired time so that each of the drugs can deliver optimal pharmacological effect. Up to now, there is no suggestion for a combination therapy in which the absorption time of an angiotensin-II-receptor blocker and HMG-CoA reductase inhibitor in vivo are controlled, considering the pharmacodynamics and pharmacokinetics of two drugs for synergistic effect by avoiding the antagonism in the liver.

Accordingly, the present invention provides a method of preventing or treating hypertension, hyperlipidemia, cardiovascular diseases, cardiopulmonary diseases, pulmonary diseases, renal disorders, or metabolic syndromes, which comprises administrating to a subject therapeutically effective amount of an angiotensin-II-receptor blocker and an HMG-CoA reductase inhibitor, wherein the angiotensin-II-receptor blocker is absorbed substantially later than the HMG-CoA reductase inhibitor.

In an embodiment, the administration can be performed such that the angiotensin-II-receptor blocker is absorbed 1.5-6 hours substantially later than the HMG-CoA reductase inhibitor.

In the above method, the angiotensin-II-receptor blocker and the HMG-CoA reductase inhibitor can be administrated in the form of a combination preparation or single preparation. For example, the combination preparation can be designed such that the release of angiotensin-II-receptor blocker is delayed substantially later than the HMG-CoA reductase inhibitor; thereby angiotensin-II-receptor blocker is absorbed 1.5-6 hours substantially later than the HMG-CoA reductase inhibitor.

Also, the present invention provides a combination preparation of an angiotensin-II-receptor blocker and an HMG-CoA reductase inhibitor for use in the combination therapy. Specifically, the present invention provides a combination preparation comprising a lag time delayed-release portion comprising an angiotensin-II-receptor blocker as an active ingredient and an immediate release portion comprising an HMG-CoA reductase inhibitor as an active ingredient.

The combination preparation of the present invention is designed so that an angiotensin-II-receptor blocker and an HMG-CoA reductase inhibitor is introduced to blood at designated times considering drug interactions between them and in-vivo drug metabolism. Drug metabolism of both the angiotensin-II-receptor blocker and the HMG-CoA reductase inhibitor are influenced by P-glycoprotein efflux transporter and cytochrome P450 enzymes; thus, the present combination preparation in which the angiotensin-II-receptor blocker and the HMG-CoA reductase inhibitor are released at different time prevents competitive inhibitions between the two drugs and side effects, as well as simultaneously provides synergistic effects for each active ingredient and convenience for taking the drugs.

Therefore, the combination therapy and the combination preparation of the present invention is beneficial for use in preventing or treating hypertension, hyperlipidemia, cardiovascular diseases, cardiopulmonary diseases, pulmonary diseases, renal disorders, or metabolic syndromes.

DETAILED DESCRIPTION OF THE INVENTION

Figure 1:
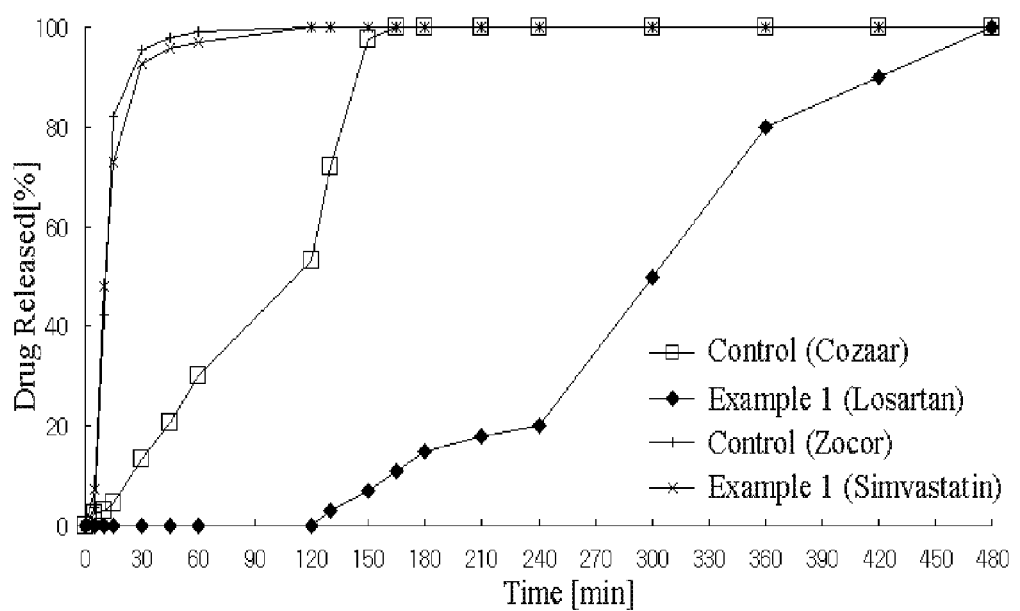
FIG. 1 is a diagram showing the comparative dissolution profiles of the combination preparation of losartan-simvastatin, prepared in Example 1, and the losartan and simvastatin components of single tablets, Cozaar® and Zocor®, as control groups.

As mentioned above, simple combination therapy of an angiotensin-II-receptor blocker and an HMG-CoA reductase inhibitor are clinically used although the simple combination therapy leads to side effects because the co-administration of the two drugs shows remarkable synergistic effect. However, when an angiotensin-II-receptor blocker and an HMG-CoA reductase inhibitor are simultaneously administrated, competitive inhibitions arises between the two drugs for P-glycoprotein efflux transporter and cytochrome P450 3A4 the in small intestine and liver, thereby reducing drug efficacy and increasing the risk of side effects. Thus, it is better for the two drugs to be absorbed at different times.

Absorption of the angiotensin-II-receptor blocker and the HMG-CoA reductase inhibitor at different times can prevent simultaneous introduction of the two drugs in the liver and competitive inhibitions between the two drugs on the metabolizing enzymes, and the efficacy of the two drugs can be maximized while the side effects of the HMG-CoA reductase inhibitor can be reduced.

The present inventors note that it is most effective to administer the HMG-CoA reductase inhibitor in the evening, since the synthesis of cholesterol actively progresses at night. The present inventors also note it is most effective to take the angiotensin-II-receptor blocker in the evening, such that it is most active in the morning that blood pressure reaches its highest level, as the angiotensin-II-receptor blocker has a duration of action of 24 hours. Therefore, it is beneficial that the two drugs are administered in the evening.

However, patients are likely to simultaneously take the two drugs, which are currently available as single preparations. Considering their drug metabolism and the side effects as shown above, it is therapeutically most beneficial to administer the HMG-CoA reductase inhibitor at first and then administer the angiotensin-II-receptor blocker after a given time.

Accordingly, the present invention provides a method of preventing or treating hypertension, hyperlipidemia, cardiovascular diseases, cardiopulmonary diseases, pulmonary diseases, renal disorders, or metabolic syndromes, which comprises administrating to a subject a therapeutically effective amount of an angiotensin-II-receptor blocker and an HMG-CoA reductase inhibitor, wherein the angiotensin-II-receptor blocker is absorbed substantially later than the HMG-CoA reductase inhibitor.

In the Example, it is confirmed that when the HMG-CoA reductase inhibitor and the angiotensin-II-receptor blocker are administered at different times, the onset and safety of the drugs are significantly improved when compared to simultaneous administration.

In an embodiment, the administration can be performed such that the angiotensin-II-receptor blocker is absorbed 1.5-6 hours substantially later than the HMG-CoA reductase inhibitor.

In the above method, the angiotensin-II-receptor blocker and the HMG-CoA reductase inhibitor can be administrated in the form of a combination preparation or single preparation. For examples, the combination preparation can be designed such that the release of angiotensin-II-receptor blocker is delayed substantially later than the HMG-CoA reductase inhibitor; thereby angiotensin-II-receptor blocker is absorbed 1.5-6 hours substantially later than the HMG-CoA reductase inhibitor.

The phrase "angiotensin-II-receptor blocker is absorbed 1.5-6 hours substantially later than the HMG-CoA reductase inhibitor" means that the angiotensin-II-receptor blocker is absorbed or metabolized in the liver or small intestine 1.5-6 hours substantially later than the HMG-CoA reductase inhibitor. The expression "substantially" means most of angiotensin-II-receptor blocker is absorbed 1.5-6 hours later than the HMG-CoA reductase inhibitor. It is better that all amounts of angiotensin-II-receptor blocker to be administrated is absorbed 1.5-6 hours later than the HMG-CoA reductase inhibitor, however, the present invention does not exclude a situation that small amounts of the angiotensin-II-receptor blocker is absorbed with the HMG-CoA reductase inhibitor.

In order for the angiotensin-II-receptor blocker to be absorbed 1.5-6 hours substantially later than the HMG-CoA reductase inhibitor, administration time or release time of the drugs can be controlled.

In the case of controlling administration time, the angiotensin-II-receptor blocker and the HMG-CoA reductase inhibitor are administered in the form of a single preparation, respectively.

If each of the angiotensin-II-receptor blocker and the HMG-CoA reductase inhibitor is administrated in the form of a single preparation, and both of them are immediate release formulations, the angiotensin-II-receptor blocker can be administrated 1.5-6 hours later than the HMG-CoA reductase inhibitor.

However, knowledge of such medication methods is not easily explained to patients. Furthermore, patients who would take such drugs are mostly elderly who are always poor and incorrect in compliance.

Thus, preferably, the angiotensin-II-receptor blocker and the HMG-CoA reductase inhibitor are administrated in the form of a combination preparation where release times of the drugs are controlled. In this case, the combination preparation can be designed such that release of angiotensin-II-receptor blocker is delayed substantially later than the HMG-CoA reductase inhibitor; thereby, angiotensin-II-receptor blocker is absorbed 1.5-6 hours substantially later than the HMG-CoA reductase inhibitor. In the present invention, as an example of the combination preparation, a combination preparation comprising a lag time delayed-release portion comprising an angiotensin-II-receptor blocker as an active ingredient and an immediate release portion comprising an HMG-CoA reductase inhibitor as an active ingredient is provided. This combination preparation will be described in detail below.

Meanwhile, it is most effective to administer the HMG-CoA reductase inhibitor in the evening because the synthesis of cholesterol actively progresses at night. Further, because the angiotensin-II-receptor blocker has duration of action of 24 hours, it is most effective to take the angiotensin-II-receptor blocker in the evening, so that it is active in the morning when blood pressure reaches a peak. Therefore, considering the biorhythms of diseases, preferably, the combination preparation can be administrated between 5 p.m. and 10 p.m. once a day.

In the present invention, any kind of known angiotensin-II-receptor blocker can be used as the angiotensin-II-receptor blocker of the present invention. The angiotensin-II-receptor blocker can be one or more components selected from the group consisting of losartan, valsartan, irbesartan, candesartan, telmisartan, eprosartan, olmesartan and pharmaceutically acceptable salts thereof, but not limited thereto.

Because the angiotensin-II-receptor blocker is used in an amount of 5-1200 mg per day for adults (adult males weighing 65-75 kg), it is used in an amount of 5-1200 mg, and preferably 8-600 mg in the combination therapy of the present invention.

In the present invention, any kinds of known HMG-CoA reductase inhibitor can be use as the HMG-CoA reductase inhibitor of the present invention. In an embodiment, the HMG-CoA reductase inhibitor can be one or more components selected from the group consisting of simvastatin, lovastatin, atorvastatin, pitavastatin, rosuvastatin, fluvastatin, pravastatin and pharmaceutically acceptable salts thereof, but not limited thereto. Because this HMG-CoA reductase inhibitor is used in an amount of 1-160 mg per day for adults, it is used in an amount of 1-160 mg, and preferably 1-80 mg, in the combination therapy of the present invention.

The present invention also provides a combination preparation comprising a lag time delayed-release portion comprising an angiotensin-II-receptor blocker as an active ingredient and an immediate release portion comprising an HMG-CoA reductase inhibitor as an active ingredient.

In order to solve the above-described problem in such a way that the angiotensin-II-receptor inhibitor as an active ingredient may not interfere with the HMG-CoA reductase inhibitor in the liver, the combination preparation of the present invention is technically designed and characterized where the HMG-CoA reductase inhibitor is formulated into an intermediate-release portion to be dissolved first, so as to be absorbed first from the small intestines; and the angiotensin-II-receptor inhibitor is formulated into a lag time delayed-release portion, to be absorbed substantially later than the HMG-CoA reductase inhibitors.

When the HMG-CoA reductase inhibitor is released ahead of the angiotensin-II-receptor blocker, it will absorbed in the small intestines before the angiotensin-II-receptor blocker and it will bind to P-glycoprotein efflux transporter and cytochrome P450 3A4 in the small intestine and liver, so that the HMG-CoA reductase inhibitor will be metabolized in the liver to inhibit the biosynthesis of cholesterol. The angiotensin-II-receptor blocker, released after that the HMG-CoA reductase inhibitor is absorbed, will be metabolized by the activated P-glycoprotein efflux transporter and cytochrome P450 3A4, so that it will be converted to active metabolites of the angiotensin-II-receptor blocker which show blood pressure-reducing effects.

Thus, the combination preparation of the present invention in which an angiotensin-II-receptor blocker and an HMG-CoA reductase inhibitor have different release rates, is designed so that the antagonism between the drugs can be prevented in order to reduce the side effects of each drugs and to achieve synergistic effects.

Furthermore, the combination preparation of the present invention provides convenience and simplicity for patients who take both angiotensin-II-receptor blocker and HMG-CoA reductase inhibitors, since the patients can take the two drugs at a single instance.

The advantages of the novel combination preparation of the present invention over the simultaneous co-administration of the two drugs may be summarized as in Table 2 below.

TABLE 2

The novel combination preparation of the present invention has the following advantages and benefits;

1) An excellent effect of lowering blood pressure.
2) An excellent effect of lowering synthesis of lipids.
3) An excellent preventive action against endothelial dysfunctions from becoming more severe.
4) Shows optimal effect at the time of the most prevalent and risky cardiovascular complications.
5) An excellent efficacy in treatment of the hypertension of non-dipper patients.
6) Significant reduction of insulin resistance in hypertensive diabetes.
7) Reduction of the time to instruct the patient on taking the medication, and realization of correct medication in view of multiple prescription methods Meanwhile, considering the time for metabolizing the HMG-CoA reductase inhibitor and the synergic effect according to the co-administration of the two drugs, it is preferred that the delayed-release time of angiotensin-II-receptor blocker is controlled in the preferable range.

In an embodiment, the combination preparation can be designed such that release of angiotensin-II-receptor blocker is delayed substantially later than the HMG-CoA reductase inhibitor, where angiotensin-II-receptor blocker is absorbed 1.5-6 hours substantially later than the HMG-CoA reductase inhibitor.

For example, when the drug delivery system of the present invention is orally administered, the HMG-CoA reductase inhibitor is released immediately, such that more than 60% of the drug is dissolved within 1 hour, and the release of the angiotensin-II-receptor blocker in the gastrointestinal tracts is sufficiently delayed, such that the absorption of angiotensin-II-receptor blocker is delayed 1.5-6 hours after the oral administration. Preferably, the combination preparation can be designed such that the HMG-CoA reductase inhibitor is released, such that more than 80% of the drug is dissolved within 1 hour, and the release of angiotensin-II-receptor blocker is substantially delayed up to 1.5-6 hours; thereby, angiotensin-II-receptor blocker is absorbed 1.5-6 hours substantially later than the HMG-CoA reductase inhibitor. In an embodiment, "the release of angiotensin-II-receptor blocker is substantially delayed up to 1.5-6 hours" means the release of the drug is controlled such that the release and absorption of the angiotensin-II-receptor blocker is less than 20% up to 1.5-6 hours.

In one embodiment, the angiotensin-II-receptor blocker is lag time delayed-released such that a dissolution rate of the angiotensin-II-receptor blocker is less than 10% up to a total of 120 minutes, and less than 20% up to a total of 240 minutes.

As described above, the combination preparation of the present invention can be beneficially used for preventing or treating hypertension, hyperlipidemia, cardiovascular diseases, cardiopulmonary diseases, pulmonary diseases, renal disorders, or metabolic syndromes.

The kinds and administration amount of angiotensin-II-receptor blocker and HMG-CoA reductase inhibitor are the same as in the above.

In the combination preparation of the present invention, the lag time delayed-release portion may comprise release-delaying materials which can achieve such purpose of releasing angiotensin-II-receptor blocker, delayed substantially later than the HMG-CoA reductase inhibitor, where angiotensin-II-receptor blocker is absorbed 1.5-6 hours substantially later than the HMG-CoA reductase inhibitor. Any release-delaying materials can be used if it can achieve such purpose. A skilled artisan can select such release-delaying materials from well-known materials.

In an embodiment, the lag time delayed-release portion may comprise one or more release-delaying materials selected from the group consisting of an enteric polymer, a water-insoluble polymer, a hydrophobic compound and a hydrophilic polymer. The release controlling material of the lag time delayed-release portion can be used in an amount of 10-500 parts by weight based on 100 parts by weight of angiotensin-II-receptor blocker. If the amount used for the release-controlling material is below the lower limit of the range, it cannot achieve sufficient release-control, and if the amount of use of angiotensin-II-receptor blocker exceeds the upper limit of the range, the drug release will be delayed, and thus a significant clinical effect cannot be obtained.

The enteric polymer means a polymer which is water-insoluble or stable under acidic condition less than pH 5.0, and is dissolved or discomposed under given pH condition more than pH 5.0.

In an embodiment, the enteric polymer may be one or a mixture of two or more selected from the group consisting of an enteric cellulose derivative, an enteric acrylate copolymer, an enteric polymethacrylate copolymer, an enteric maleate copolymer, an enteric polyvinyl derivative, and shellac.

For example, the enteric cellulose derivative includes hypromellose acetate succinate, hypromellose phthalate, hydroxylmethylethyl cellulose phthalate, cellulose acetate phthalate, cellulose acetate succinate, cellulose acetate maleate, cellulose benzoate phthalate, cellulose propionate phthalate, methyl cellulose phthalate, carboxymethylethyl cellulose, ethylhydroxyethyl cellulose phthalate and methylhydroxyethyl cellulose etc.

The enteric acrylate copolymer includes, for example, styrene-acrylic acid copolymer, butyl acrylate-styrene-acrylic acid copolymer, methyl acrylate-metacrylate-octyl acrylate copolymer etc.

Also, for example, enteric polymethacrylate copolymer includes poly(methacrylic acid, methyl methacrylate) 1:1 (e.g. Eudragit L 100, Eudragit L 12.5), poly(methacrylic acid, ethyl acrylate) 1:1 (e.g. Acryl-EZE, Acryl-EZE MP, Eudragit L30 D-55, Eudragit L 100-55, Eastacryl 30D, Kolicoat MAE 30 D, Kolicoat MAE 30 DP), poly(methacrylic acid, methyl methacrylate) 1:2 (e.g. Eudragit S 100, Eudragit S 12.5), poly(methyl acrylate, methyl methacrylate, methacrylic acid) 7:3:1 (e.g. Eudragit FS 30D), etc.

The enteric maleate copolymer includes, for example, vinyl acetate-maleic acid anhydride copolymer, styrene-maleic acid anhydride copolymer, styrene-maleic acid monoester copolymer, vinyl methyl ether-maleic acid anhydride copolymer, ethylene-maleic acid anhydride copolymer, vinyl buthyl ether-maleic acid anhydride copolymer, acrylonitrile-methyl acrylate-maleic acid anhydride copolymer, butyl acrylate-styrene-maleic acid anhydride copolymer etc.

Further, the enteric polyvinyl derivative includes, for example, polyvinyl alcohol phthalate, polyvinyl butyrate phthalate, polyvinyl acetate phthalate etc.

Preferably, the enteric polymer may be one or a mixture of two or more selected from the group consisting of Hypromellose acetate succinate, Hypromellose phthalate, poly(methacrylic acid, methyl methacrylate) 1:1, poly(methacrylic acid, ethyl acrylate) 1:1, poly(methacrylic acid, methymethacrylate) 1:2, poly(methylacrylate, methyl methacrylate, methacrylic acid) 7:3:1, polyvinyl acetate phthalate, cellulose acetate phthalate, cellulose propionate phthalate and shellac.

The water-insoluble polymer may be one or a mixture of two or more selected from polyvinyl acetate, water-insoluble polymethacrylate copolymers, such as poly(ethyl acrylate, methyl methacrylate) and poly(ethylacrylate, methyl methacrylate, trimethylaminoethyl methacrylate chloride), ethyl cellulose and cellulose acetate, which are pharmaceutically acceptable. The hydrophobic compound may be selected from fatty acids, fatty acid esters, fatty acid alcohols, waxes and inorganic materials. Specifically, it may be one or a mixture of two or more selected from: fatty acids or fatty acid esters including glyceryl palmitostearate, glyceryl stearate, glyceryl behenate, cetyl palmitate, glyceryl monooleate and stearic acid; fatty acid alcohols including cetostearyl alcohol, cetyl alcohol and stearyl alcohol; waxes including Carnauba wax, beeswax and microcrystalline wax; and inorganic materials including talc, precipitated calcium carbonate, dibasic calcium phosphate, zinc oxide, titanium oxide, kaolin, bentonite, montmorillonite and veegum.

The hydrophilic polymer may be selected from polysaccharides, cellulose derivatives, gums, proteins, polyvinyl derivatives, polymethacrylate copolymers, polyethylene derivatives and carboxyvinyl polymers. Specifically, it may be one or a mixture from among: saccharides including dextrin, polydextrin, dextran, pectin and pectin derivatives, alginate, polygalacturonic acid, xylan, arabinoxylan, arabinogalactan, starch, hydroxypropyl starch, amylose and amylopectin; cellulose derivatives including hypromellose (hydroxypropylmethyl cellulose), hydroxypropyl cellulose, hydroxymethyl cellulose, hydroxyethyl cellulose, methyl cellulose, carboxymethyl cellulose sodium, and hydroxyethylmethylcellulose; gums including guar gum, locust bean gum, tragacanth, carrageenan, acacia gum, Arabic gum, gellan gum, and xanthan gum; proteins including gelatin, casein and zein; polyvinyl derivatives including polyvinyl alcohol, poly(vinyl pyrrolidone) and polyvinylacetaldiethylaminoacetate; polymethacrylate copolymers including poly(butyl methacrylate, (2-dimethylaminoethyl)methacrylate, methylmethacrylate) copolymers; polyethylene derivatives including polyethylene glycol and polyethylene oxide; and carboxyvinyl polymers such as carbomer.

Within a reasonable range, not impairing the effects of the present invention, pharmaceutically acceptable additives such as diluents, binders, disintegrants, lubricants, stabilizers, colorants and fragrance can be used. For example, dilutes including starch, microcrystalline cellulose, lactose, glucose, mannitol, alginate, alkaline earth metal salts, clay, polyethylene glycol and dicalcium phosphate may be used, and lubricants including talc, alkaline-earth metal stearate such as calcium stearate, magnesium stearate or zinc stearate, lauryl sulfate, hydrogenated vegetable oil, sodium benzoate, sodium stearyl fumarate, glyceryl monostearate and polyethyleneglycol 4000 may be used, but the scope of additives for use in the present invention is not limited thereto. Examples of binders may include starch, microcrystalline cellulose, highly dispersible silica, mannitol, lactose, polyethylene glycol, polyvinyl pyrrolidone, hydroxypropyl methylcellulose, hydroxypropylcellulose, natural gum, synthetic gum, Copovidone and gelatin. Examples of disintegrants may include starches such as sodium starch glycolate, corn starch, potato starch pregelatinized starch or modified starch, clays such as bentonite, montmorillonite or veegum, microcrystalline cellulose, low-substitution hydroxypropylcellulose, hydroxypropylcellulose, sodium alginate, cross-linked cellulose such as croscarmellose sodium, gums such as guar gum or xanthan gum, crosslinked polymers such as crospovidone, and materials such as sodium bicarbonate or citric acid. These disintegrants may be used alone or in a mixture of two or more. Examples of lubricants may include talc, magnesium stearate, alkaline metal stearates such as calcium or zinc stearate, lauryl sulfate, hydrogenated vegetable oil, sodium benzoate, sodium stearyl fumarate, glyceryl monostearate and polyethyleneglycol 4000. Examples of stabilizers may include ascorbic acid, citric acid, butylatyed hydroxyanisole, butylated hydroxytoluene and tocopherol derivatives. In addition, pharmaceutically acceptable additives selected from colorants, fragrances and the like may be used in the present invention.

The lag time delayed-release portion of the novel combination preparation of the present invention may consist of a discontinuous phase comprising of particles or granules obtained by mixing, granulating or coating an angiotensin-II-receptor blocker, release-delaying materials and a pharmaceutically acceptable conventional excipient. Preferably, the lag time delayed-release portion of the combination preparation may consist of a discontinuous phase comprising of particles or granules of an angiotensin-II-receptor blocker and a pharmaceutically acceptable conventional excipient, coated with release-delaying materials.

The immediate release portion of the combination preparation of the present invention may consists of particles or granules by subjecting an HMG-CoA reductase inhibitor (represented by simvastatin or atorvastatin), as an active ingredient, together with a pharmaceutically acceptable excipient to conventional processes for producing oral solid drugs, such as mixing, kneading, drying and granulation.

The formulation form of the combination preparation according to the present invention is not limited specifically. For example, the combination preparation may be in the form of a two-phase matrix tablet, a two-phase matrix capsule, a multilayer tablet, or a dry-coated tablet.

In an embodiment, the present combination preparation may be a two-phase matrix tablet or a two-phase matrix capsule, which comprises granules constituting the lag time delayed-release portion and granules constituting the immediate release portion. As explained above, a two-phase matrix formulation can be prepared by adding pharmaceutically acceptable additives to the compositions constituting the lag time delayed-release portion and the immediate release portion and compressing the mixture into tablets or filling the mixture in capsules.

In another embodiment, the present combination preparation may be a multilayer tablet in which the lag time delayed-release portion and immediate release portion form a multilayer. A multilayer tablet that shows immediate release and lag time delayed-release according to each layer, can be obtained by mixing granules which constitute the lag time delayed-release portion and the immediate release portion with pharmaceutical excipients, and compressing the mixture using a multiple tableting machine into a two-layered or three-layered tablet having parallel layers.

In still another embodiment, the present combination preparation may be in the form of a dry-coated tablet having (i) an inner core comprising the lag time delayed-release portion and (ii) an outer layer comprising the immediate release portion and covering the outer surface of the inner core. The dry-coated tablet can be obtained by mixing a granule constituting the lag time delayed-release portion with a pharmaceutical excipient, tableting the mixture to form a core tablet, mixing a granule constituting the immediate release portion with a pharmaceutical excipient, and compressing the mixture onto the surface of the core tablet to form an outer layer.

If necessary, a film coating layer may be formed on the outer surface of the combination preparation of the present invention. That is, the combination preparation of the present invention comprising the angiotensin-II-receptor blocker and the HMG-CoA reductase inhibitor may also be used in the form of a core tablet having no coating layer, and if a coating layer is formed on the surface of the tablet containing said active ingredients so as to form a coated tablet, the stability of the active ingredients can be further ensured. The coating layer can be formed according to a suitable method selected from methods capable of forming the coating layer on the surface of the tablet, and examples of such methods include a fluidized bed coating method and a pan coating method. The pan coating method is preferably used.

The coating layer can be formed using a coating agent, a coating aid or a mixture thereof. Specifically, as the coating agent in the coating layer, one or a mixture of one or more selected from cellulose derivatives, sugar derivatives, polyvinyl derivatives, waxes, fats and gelatin may be used, and as the coating aid, one or a mixture of two or more selected from polyethylene glycol, ethyl cellulose, glycerides, titanium dioxide and diethyl phthalate may be used.

When the coated tablet is prepared, the coating layer is preferably included in an amount of 0.5-15 wt % based on the total weight of the tablet.

The above-described combination preparation of the present invention comprising the angiotensin-II-receptor blocker and the HMG-CoA reductase inhibitor as active ingredients is a dosage unit of two types of drugs, thus it can be administered only one time in the evening. Compared to the case in which single formulations containing the active ingredients are administered simultaneously, the administration of the dosage is very simple so that convenience and compliance of patients is high. Also, because antagonism between the drugs does not occur, side effects resulting from such antagonism can be reduced or eliminated. In addition, the drugs show a synergistic effect on blood pressure control and lipid control at the same time.

The advantages and features of the present invention and the method of revealing them will be explicit from the following examples described in detail. However, it is to be distinctly understood that the present invention is not limited thereto but may be otherwise variously embodied and practiced. It is obvious that the following examples are to complete the disclosure of the invention and to indicate the scope of the present invention to a skilled artisan completely, and the present invention will be defined only by the scope of the claims.

EXAMPLES

Examples 1 to 13

Preparation of Dry-Coated Tablets

1) Preparation of Lag Time Delayed-Release Inner-Core Tablets Containing Angiotensin-II-Receptor Blocker In Example 1, to prepare the losartan lag time delayed-release inner-core tablets, as shown in Tables 3, losartan potassium, microcrystalline cellulose, pregelatinized starch, copovidone and light anhydrous silicic acid were sieved through a No. 35 sieve and mixed with each other in a high-speed mixer for 5 minutes to prepare a mixture. Magnesium stearate was mixed with the mixture for 4 minutes. The resulting mixture was compressed into inner-core tablets using a rotary tableting machine (MRC-33, Sejong Machinery Co., Korea). A coating solution having the compositions and contents shown in Table 3 were prepared. The inner-core tablets thus prepared were placed in a Hi-coater (SFC-30N, Sejong Machinery Co., Korea), and coated with the coating solution to prepare a lag time delayed-release inner-core tablets product according to conventional methods of tablet film coating.

In Examples 2~13, lag time delayed-release inner-core tablets containing losartan potassium, candesartan, telmisartan, or olmesartan having the compositions and contents shown in Table 3 was prepared in the same manner as Example 1.

2) Preparation of the Immediate Release Layer Containing HMG-CoA Reductase Inhibitor In Example 1, to prepare the HMG-CoA reductase inhibitor layer, shown in Table 3, HMG-CoA reductase inhibitor simvastatin and excipients including microcrystalline cellulose, lactose, corn starch and starch glycolate sodium, were sieved through a No. 35 sieve and mixed with each other in a high-speed mixer. Meanwhile, hydroxypropylcellulose and citric acid were dissolved in water to prepare a binder solution. The binder solution was placed in the high-speed mixer with said mixture and kneaded. After completion of the kneading process, the kneaded material was granulated through a No. 18 sieve using an oscillator, and the granules were dried in a hot-water dryer at 60° C. After completion of the drying process, the granules were sieved through a No. 20 sieve. Butylated hydroxyanisole was mixed with the sieved material in a double cone mixer. Magnesium stearate was finally mixed with the mixture in the double cone mixer.

In Examples 2 to 13, the immediate release products containing simvastatin, lovastatin, or atorvastatin having the compositions and contents shown in Table 3 were prepared in the same manner as Example 1.

3) Tableting and Coating

Dry-coated tablets, having the angiotensin-II-receptor blocker-containing inner-core tablet as the core layer and the HMG-CoA reductase inhibitor-containing composition as the outer layer, were prepared using a press tableting machine (RUD-1: Kilian). Meanwhile, Hypromellose 2910 (hydroxypropyl methyl cellulose 2910), titanium oxide and talc were dissolved and dispersed in 75% ethanol to prepare a coating solution having the composition and contents as shown in Table 3. Said dry-coated tablets were placed in a Hi-coater (SFC-30N, Sejong Machinery Co., Korea), in which the tablets were then coated with the coating solution, thus preparing dry-coated tablets.

Examples 14 to 17

Preparation of 2-Phase Matrix Tablets

1) Preparation of Angiotensin-II-Receptor Blocker Lag Time Delayed-Release Granules To prepare angiotensin-II-receptor blocker lag time delayed-release granules in Example 14, eprosartan, microcrystalline cellulose, pregelatinized starch, and light anhydrous silicic acid were sieved through a No. 35 sieve and mixed with each other in a high-speed mixer for 5 minutes to prepare a mixture. Meanwhile, copovidone was dissolved in purified water to prepare a binder solution. The binder solution was added to the mixture, which was then kneaded, granulated and dried. The dried material was placed in a fluidized bed coater (GPCG-1, Glatt, Germany). Meanwhile, hypromellose and Eudragit L 100-55 (Evonik Degussa GmbH) were dissolved and dispersed in ethanol to prepare a coating solution. The dried granules were coated with the coating solution in the fluidized bed coater (GPCG-1, Glatt, Germany), thus preparing eprosartan delayed-release granules.

In Example 15, losartan potassium, microcrystalline cellulose, crospovidone, and sodium chloride were sieved through a No. 35 sieve and mixed with each other in a high-speed mixer for 5 minutes to prepare a mixture. Meanwhile, hydroxypropylcellulose was dissolved in purified water to prepare a binder solution. The binder solution was added to the mixture, which was then kneaded, granulated and dried. The dried material was placed in a fluidized bed coater (GPCG-1, Glatt, Germany). Meanwhile, cellulose acetate (32% acetyl group), cellulose acetate (39.8%) and hypromellose were dissolved and dispersed in 220 mg of ethanol and 980 mg of methylene chloride to prepare a coating solution. The dried granules were coated with the coating solution in the fluidized bed coater (GPCG-1, Glatt, Germany), thus preparing losartan lag time delayed-release granules.

In Example 16, losartan potassium and microcrystalline cellulose were sieved through a No. 35 sieve and mixed with each other in a high-speed mixer for 5 minutes to prepare a mixture. The mixture was placed in a fluidized bed coater (GPCG-1, Glatt, Germany), coated with a coating solution in which hypromellose was dissolved in 80% ethanol, and further coated with a coating solution in which hypromellose phthalate was dissolved in 80% ethanol, thereby preparing losartan delayed-release granules.

In Example 17, losartan potassium and microcrystalline cellulose were sieved through a No. 35 sieve and mixed with each other in a high-speed mixer for 5 minutes to prepare a mixture. The mixture was placed in a fluidized bed coater (GPCG-1, Glatt, Germany), and coated with a coating solution in which Kollicoat SR30D (BASF AG) was diluted in purified water.

2) Preparation of Simvastatin Immediate Release Granules

In Examples 14 and 17, to prepare simvastatin immediate release granules, as shown in Table 4 below, simvastatin, microcrystalline cellulose and mannitol were sieved through a No. 35 sieve and mixed with each other in a high-speed mixer. Meanwhile, hydroxypropylcellulose and citric acid were dissolved in water to prepare a binder solution, which was then kneaded with said mixture. After kneading, the kneaded material was granulated through a No. 18 sieve using an oscillator, and the granules were dried in a hot-water dryer at 60° C. After drying, the granules were sieved through a No. 20 sieve. The sieved material was mixed with butylated hydroxyanisole.

In Examples 15 and 16, to prepare simvastatin immediate release granules, as shown in Table 4 below, simvastatin, microcrystalline cellulose, lactose and corn starch were sieved through a No. 35 sieve and mixed with each other in a high-speed mixer. Meanwhile, hydroxypropylcellulose and citric acid were dissolved in water to prepare a binder solution, which was then kneaded with said mixture. After kneading, the kneaded material was granulated through a No. 18 sieve using an oscillator, and the granules were dried in a hot-water dryer at 60° C. After drying, the granules were sieved through a No. 20 sieve. The sieved material was mixed with butylated hydroxyanisole.

3) Post-Mixing, Tableting and Coating

The above-prepared angiotensin-II-receptor blocker lag time delayed-release granules and simvastatin immediate release granules were mixed with each other in a double cone mixer. The mixture was mixed with starch glycolate sodium and finally mixed with magnesium stearate. The resulting mixture was compressed into tablets using a rotary tableting machine (MRC-33, Sejong Machinery Co., Korea). Meanwhile, hypromellose 2910, hydroxypropylcellulose, titanium oxide and talc were dissolved and dispersed in 80% ethanol to prepare a coating solution. Said tablets were coated with the coating solution in a Hi-coater (SFC-30N, Sejong Machinery Co., Korea) to form a film coating layer, thus preparing two-phase matrix tablets.

Examples 18 to 27

Preparation of Multilayered Tablets

1) Preparation of the Lag Time Delayed-Release Layer of Angiotensin-II-Receptor Blocker In Examples 18, 21, 23, 24 and 26, the lag time delayed-release granules of angiotensin-II-receptor blocker having the compositions and contents shown in Table 4 were prepared in the same manner as Example 15. The prepared lag time delayed-release granules of angiotensin-II-receptor blocker were mixed with magnesium stearate for 4 minutes.

In Examples 19, 22, 25 and 27, the lag time delayed-release granules of angiotensin-II-receptor blocker having the composition and contents shown in Table 4 were prepared in the same manner as Example 16. The prepared lag time delayed-release granules of angiotensin-II-receptor blocker were mixed with magnesium stearate for 4 minutes.

In Example 20, the lag time delayed-release granules of angiotensin-II-receptor blocker having the composition and contents shown in Table 4 were prepared in the same manner as Example 17. The prepared lag time delayed-release granules of angiotensin-II-receptor blocker were mixed with magnesium stearate for 4 minutes.

2) Preparation of the HMG-CoA Reductase Inhibitor Immediate Release Layer

In order to prepare an HMG-CoA reductase inhibitor layer, a mixture of HMG-CoA reductase inhibitor and excipients having the composition and contents as shown in Table 4 was prepared in the same manner as Example 14. The mixture was mixed with starch glycolate sodium and finally mixed with magnesium stearate.

3) Tableting and Coating

A multilayer tableting machine (MRC-37T, Sejong Machinery Co., Korea) was used. The HMG-CoA reductase inhibitor-containing immediate release composition was placed in a first powder feeder, and the angiotensin-II-receptor blocker-containing lag time delayed-release layer composition was placed in a second powder feeder. The compositions in the feeders were compressed into tablets in conditions in which interlayer incorporation could be minimized. Meanwhile, hypromellose 2910, hydroxypropylcellulose, titanium oxide and talc were dissolved and dispersed in 80% ethanol to prepare a coating solution. Said tablets were coated with the coating solution in a Hi-coater (SFC-30N, Sejong Machinery Co., Korea) to form a coating layer, thus preparing multilayered tablets.

Examples 28 and 29

Preparation of Capsules

1) Preparation of Angiotensin-II-Receptor Blocker Lag Time Delayed-Release Granules In Examples 28 and 29, losartan lag time delayed-release granules were prepared in the same manner as Examples 15 and 16, respectively.

2) Preparation of Immediate Release Granules Containing HMG-CoA Reductase Inhibitor Immediate release granules containing HMG-CoA reductase inhibitor were prepared in the same manner as Example 14.

3) Mixing and Filling in Capsule

The compositions, obtained in the steps 1) and 2), were mixed with each other in a double cone mixer. The mixture was mixed with starch glycolate sodium in the double cone mixer. Then, the mixture was finally mixed with magnesium stearate. The resulting mixture was placed in a powder feeder and used to fill in capsules using a capsule filling machine, thus preparing a capsule-type combination preparation.

Examples 30~38

Preparation of Dry-Coated Tablets

1) Preparation of Lag Time Delayed-Release Inner-Core Tablets Containing Angiotensin-II-Receptor Blocker In Examples 30~38, to prepare losartan lag time delayed-release inner-core tablets, as shown in Table 5, losartan potassium, microcrystalline cellulose, light anhydrous silicic acid, low-substituted hydroxypropylcellulose and crospovidone were sieved through a No. 35 sieve and mixed with each other in a high-speed mixer for 5 minutes to prepare a mixture. Meanwhile, povidone was dissolved in ethanol to prepare a binder solution. The binder solution was added to the mixture, which was then kneaded, granulated and dried. Magnesium stearate was mixed with the dried material for 4 minutes. The resulting mixture was compressed into inner-core tablets using a rotary tableting machine (MRC-33, Sejong Machinery Co., Korea). The prepared inner-core tablets were placed in a Hi-coater (SFC-30N, Sejong Machinery Co., Korea), and coated with Opadry (03B28796, Colorcon). Meanwhile, a coating solution having the compositions and contents shown in Table 5 were prepared. The coated inner-core tablets were placed in a Hi-coater (SFC-30N, Sejong Machinery Co., Korea), and coated with the coating solution to prepare a lag time delayed-release inner-core tablets product according to conventional methods of tablet film coating.

2) Preparation of the Immediate Release Layer Containing HMG-CoA Reductase Inhibitor In Example 1, to prepare an HMG-CoA reductase inhibitor layer, HMG-CoA reductase inhibitor atorvastatin and excipients including calcium carbonate, low-substituted hydroxypropylcellulose (LH-22, Shin-Etsu), polysorbate 80, mannitol and crospovidone were sieved through a No. 35 sieve and mixed with each other in a high-speed mixer. Meanwhile, hydroxypropylcellulose was dissolved in 80% ethanol to prepare a binder solution. The binder solution was placed in the high-speed mixer with said mixture and kneaded. After completion of the kneading process, the kneaded material was granulated through a No. 18 sieve using an oscillator, and the granules were dried in a hot-water dryer at 60° C. After completion of the drying process, the granules were sieved through a No. 20 sieve. Microcrystalline cellulose, light anhydrous silicic acid, low-substituted hydroxypropylcellulose (LH-11, Shin-Etsu) and crocarmellose sodium were mixed with the sieved material in a double cone mixer. Magnesium stearate was finally mixed with the mixture in the double cone mixer.

In Examples 31~38, the immediate release layer containing HMG-CoA reductase inhibitor having the composition and contents shown in Table 5, were prepared in the same manner as Example 30.

3) Tableting and Coating

Dry-coated tablets, having the angiotensin-II-receptor blocker core layer and the HMG-CoA reductase inhibitor outer layer, were prepared using a press tableting machine (RUD-1: Kilian). Opadry of Table 5 was dissolved and dispersed in 90% ethanol to prepare a coating solution. The above prepared dry-coated tablets were coated with the coating solution using a Hi-coater (SFC-30N, Sejong Machinery Co., Korea).

TABLE 3

| | | Composition ratio(mg/tablet) Examples | | | | | | |
|---|---|---|---|---|---|---|---|---|
| | Components | 1 | 2 | 3 | 4 | 5 | 6 | 7 |
| lag time Delayed-release layer | Losartan potassium | 50.0 | 50.0 | 50.0 | 50.0 | 50.0 | 50.0 | 50.0 |
| | Candesartan | | | | | | | |
| | Telmisartan | | | | | | | |
| | Olmesartan | | | | | | | |
| | Microcrystalline cellulose | 14.0 | 14.0 | 14.0 | 14.0 | 14.0 | 14.0 | 14.0 |
| | Pregelatinized starch | 10.0 | 10.0 | 10.0 | 10.0 | 10.0 | 10.0 | 10.0 |
| | Copovidone | 4.5 | 4.5 | 4.5 | 4.5 | 4.5 | 4.5 | 4.5 |
| | light anhydrous silicic acid | 1.0 | 1.0 | 1.0 | 1.0 | 1.0 | 1.0 | 1.0 |
| | crospovidone | | | | | | 4.0 | 8.0 |
| | Magnesium stearate | 1.5 | 1.5 | 1.5 | 1.5 | 1.5 | 1.5 | 1.5 |
| lag time delayed-release coating layer | hypromellose | 0.8 | | | | | | |
| | ethylcellulose | | 8.0 | 12.0 | 16.0 | 20.0 | 16.0 | 16.0 |
| | Eudragit L100-55 | 8.0 | 8.0 | 8.0 | 8.0 | 8.0 | 8.0 | 8.0 |
| Immediate release layer | simvastatin | 20.0 | 20.0 | 20.0 | 20.0 | 20.0 | 20.0 | 20.0 |
| | lovastain | | | | | | | |
| | atorvastatin | | | | | | | |
| | Microcrystalline cellulose | 95.0 | 95.0 | 95.0 | 95.0 | 95.0 | 95.0 | 95.0 |
| | lactose | 268.0 | 268.0 | 268.0 | 268.0 | 268.0 | 268.0 | 268.0 |
| | corn starch | 50.0 | 50.0 | 50.0 | 50.0 | 50.0 | 50.0 | 50.0 |
| | Starch glycolate sodium | 15.0 | 15.0 | 15.0 | 15.0 | 15.0 | 15.0 | 15.0 |
| | Butylated hydroxyanisole | 0.35 | 0.35 | 0.35 | 0.35 | 0.35 | 0.35 | 0.35 |
| | Hydroxypropyl cellulose | 10.0 | 10.0 | 10.0 | 10.0 | 10.0 | 10.0 | 10.0 |
| | citric acid | 6.5 | 6.5 | 6.5 | 6.5 | 6.5 | 6.5 | 6.5 |
| | Magnesium stearate | 5.05 | 5.05 | 5.05 | 5.05 | 5.05 | 5.05 | 5.05 |
| coating layer | hypromellose2910 | 15.8 | 15.8 | 15.8 | 15.8 | 15.8 | 15.8 | 15.8 |
| | Titanium oxide | 2.3 | 2.3 | 2.3 | 2.3 | 2.3 | 2.3 | 2.3 |
| | talc | 1.5 | 1.5 | 1.5 | 1.5 | 1.5 | 1.5 | 1.5 |
| total | | 579.3 | 586.5 | 590.5 | 594.5 | 598.5 | 598.5 | 602.5 |

TABLE 3-continued

| | Components | 8 | 9 | 10 | 11 | 12 | 13 |
|---|---|---|---|---|---|---|---|
| lag time Delayed-release layer | Losartan potassium | 50.0 | 50.0 | 50.0 | | | |
| | Candesartan | | | | 16.0 | | |
| | Telmisartan | | | | | 40.0 | |
| | Olmesartan | | | | | | 20.0 |
| | Microcrystalline cellulose | 14.0 | 14.0 | 14.0 | 14.0 | 14.0 | 14.0 |
| | Pregelatinized starch | 10.0 | 10.0 | 10.0 | 10.0 | 10.0 | 10.0 |
| | Copovidone | 4.5 | 4.5 | 4.5 | 4.5 | 4.5 | 4.5 |
| | light anhydrous silicic acid | 1.0 | 1.0 | 1.0 | 1.0 | 1.0 | 1.0 |
| | crospovidone | 12.0 | | | | | |
| | Magnesium stearate | 1.5 | 1.5 | 1.5 | 1.5 | 1.5 | 1.5 |
| lag time delayed-release coating layer | hypromellose | | 0.8 | 0.8 | 0.5 | 0.7 | 0.5 |
| | ethylcellulose | 16.0 | | | | | |
| | Eudragit L100-55 | 8.0 | 8.0 | 8.0 | 4.7 | 7.1 | 5.1 |
| Immediate release layer | simvastatin | 20.0 | | | 20.0 | 20.0 | 20.0 |
| | lovastain | | 20.0 | | | | |
| | atorvastatin | | | 20.0 | | | |
| | Microcrystalline cellulose | 95.0 | 95.0 | 95.0 | 95.0 | 95.0 | 95.0 |
| | lactose | 268.0 | 268.0 | 268.0 | 268.0 | 268.0 | 268.0 |
| | corn starch | 50.0 | 50.0 | 50.0 | 50.0 | 50.0 | 50.0 |
| | Starch glycolate sodium | 15.0 | 15.0 | 15.0 | 15.0 | 15.0 | 15.0 |
| | Butylated hydroxyanisole | 0.35 | 0.35 | 0.35 | 0.35 | 0.35 | 0.35 |
| | Hydroxypropyl cellulose | 10.0 | 10.0 | 10.0 | 10.0 | 10.0 | 10.0 |
| | citric acid | 6.5 | 6.5 | 6.5 | 6.5 | 6.5 | 6.5 |
| | Magnesium stearate | 5.05 | 5.05 | 5.05 | 5.05 | 5.05 | 5.05 |
| coating layer | hypromellose2910 | 15.8 | 15.8 | 15.8 | 18.3 | 19.2 | 18.4 |
| | Titanium oxide | 2.3 | 2.3 | 2.3 | 2.7 | 2.9 | 2.8 |
| | talc | 1.5 | 1.5 | 1.5 | 1.9 | 1.9 | 1.8 |
| total | | 606.5 | 579.3 | 579.3 | 545.0 | 572.7 | 549.5 |

Eudragit L100-55: Methacrylic acid copolymer, type C, Evonik Degussa GmbH

TABLE 4

| | Components | 14 | 15 | 16 | 17 | 18 | 19 | 20 | 21 | 22 | 23 | 24 | 25 | 26 | 27 | 28 | 29 |
|---|---|---|---|---|---|---|---|---|---|---|---|---|---|---|---|---|---|
| lag time Delayed-release layer | Losartan potassium | | 50.0 | 50.0 | 50.0 | 50.0 | 50.0 | 100.0 | | | | 50.0 | 50.0 | 50.0 | 50.0 | 50.0 | 50.0 |
| | eprosartan | 600.0 | | | | | | | | | | | | | | | |
| | valsartan | | | | | | | | 80.0 | 80.0 | | | | | | | |
| | Irbesartan | | | | | | | | | | 150.0 | | | | | | |
| | Microcrystalline cellulose | 60.0 | 25.0 | 137.0 | 123.0 | 25.0 | 137.0 | 123.0 | 40.0 | 219.2 | 75.0 | 25.0 | 137.0 | 25.0 | 137.0 | 25.0 | 137.0 |
| | Pregelatinized starch | 40.0 | | | | | | | | | | | | | | | |
| | Copovidone | 18.0 | | | | | | | | | | | | | | | |
| | light anhydrous silicic acid | 4.0 | | | | | | | | | | | | | | | |
| | crospovidone | | 50.0 | | | 50.0 | | | 80.0 | | 150.0 | 50.0 | | 50.0 | | 50.0 | |
| | Hydroxypropyl cellulose | | 5.0 | | | 5.0 | | | 8.0 | | 15.0 | 5.0 | | 5.0 | | 5.0 | |
| | Sodium chloride | | 25.0 | | | 25.0 | | | 40.0 | | 75.0 | 25.0 | | 25.0 | | 25.0 | |
| | Magnesium stearate | 6.0 | | | | 3.0 | 3.0 | 3.0 | 4.8 | 4.8 | 9.0 | 3.0 | 3.0 | 3.0 | 3.0 | | |

TABLE 4-continued

| | Components | 14 | 15 | 16 | 17 | 18 | 19 | 20 | 21 | 22 | 23 | 24 | 25 | 26 | 27 | 28 | 29 |
|---|---|---|---|---|---|---|---|---|---|---|---|---|---|---|---|---|---|
| lag time delayed-release coating layer | hypromellose | 2.0 | 2.0 | 4.0 | | 2.0 | 4.0 | | 3.2 | 6.4 | 6.0 | 2.0 | 4.0 | 2.0 | 4.0 | 2.0 | 4.0 |
| | hypromellose-phthalate | | | 6.0 | | | 6.0 | | | 9.6 | | | 6.0 | | 6.0 | | 6.0 |
| | Cellulose acetate (acetyl group 32%) | | 20.0 | | | 20.0 | | | 32.0 | | | 60.0 | 20.0 | | 20.0 | 20.0 | |
| | Cellulose acetate (acetyl group 39.8%) | | 20.0 | | | 20.0 | | | 32.0 | | | 60.0 | 20.0 | | 20.0 | 20.0 | |
| | Eudragit L100-55 | 20.0 | | | | | | | | | | | | | | | |
| | Kollicoat SR30D | | | | 24.0 | | | 48.0 | | | | | | | | | |
| Immediate release layer | simvastatin | 20.0 | 20.0 | 20.0 | 20.0 | 20.0 | 20.0 | 20.0 | 20.0 | 20.0 | 20.0 | | | | | 20.0 | 20.0 |
| | lovastatin | | | | | | | | | | | 20.0 | 20.0 | | | | |
| | atorvastatin | | | | | | | | | | | | | 20.0 | 20.0 | | |
| | Microcrystalline cellulose | 57.0 | 95.0 | 95.0 | 57.0 | 57.0 | 57.0 | 57.0 | 57.0 | 57.0 | 57.0 | 57.0 | 57.0 | 57.0 | 57.0 | 57.0 | 57.0 |
| | mannitol | 112.5 | | | 112.5 | 112.5 | 112.5 | 112.5 | 112.5 | 112.5 | 112.5 | 112.5 | 112.5 | 112.5 | 112.5 | 112.5 | 112.5 |
| | lactose | | 258.0 | 268.0 | | | | | | | | | | | | | |
| | corn starch | | | 50.0 | | | | | | | | | | | | | |
| | Starch glycolate sodium | 2.0 | 15.0 | 15.0 | 2.0 | 2.0 | 2.0 | 2.0 | 2.0 | 2.0 | 2.0 | 2.0 | 2.0 | 2.0 | 2.0 | 2.0 | 2.0 |
| | Butylated hydroxyanisole | 0.1 | 0.35 | 0.35 | 0.1 | 0.1 | 0.1 | 0.1 | 0.1 | 0.1 | 0.1 | 0.1 | 0.1 | 0.1 | 0.1 | 0.1 | 0.1 |
| | Hydroxypropyl cellulose | 5.0 | 10.0 | 10.0 | 5.0 | 5.0 | 5.0 | 5.0 | 5.0 | 5.0 | 5.0 | 5.0 | 5.0 | 5.0 | 5.0 | 5.0 | 5.0 |
| | citric acid | 2.0 | 6.5 | 6.5 | 2.0 | 2.0 | 2.0 | 2.0 | 2.0 | 2.0 | 2.0 | 2.0 | 2.0 | 2.0 | 2.0 | 2.0 | 2.0 |
| | Magnesium stearate | 4.5 | 5.05 | 5.05 | 4.5 | 1.5 | 1.5 | 1.5 | 1.5 | 1.5 | 1.5 | 4.5 | 1.5 | 1.5 | 1.5 | 4.5 | 4.5 |
| coating layer | hypromellose2910 | 33.4 | 2.6 | 2.6 | 2.6 | 2.6 | 2.6 | 2.6 | 2.6 | 2.6 | 2.6 | 2.6 | 2.6 | 2.6 | 2.6 | | |
| | Hydroxypropyl cellulose | | 2.6 | 2.6 | 2.6 | 2.6 | 2.6 | 2.6 | 2.6 | 2.6 | 2.6 | 2.6 | 2.6 | 2.6 | 2.6 | | |
| | Titanium oxide | 5.1 | 2.3 | 2.3 | 2.3 | 2.3 | 2.3 | 2.3 | 2.3 | 2.3 | 2.3 | 2.3 | 2.3 | 2.3 | 2.3 | | |
| | talc | 3.3 | 1.5 | 1.5 | 1.5 | 1.5 | 1.5 | 1.5 | 1.5 | 1.5 | 1.5 | 1.5 | 1.5 | 1.5 | 1.5 | | |
| capsule | capsule(size 0) | | | | | | | | | | | | | | | 97 | 97 |
| | total | 994.9 | 665.9 | 675.9 | 409.1 | 409.1 | 409.1 | 483.1 | 529.1 | 529.1 | 812.1 | 409.1 | 409.1 | 409.1 | 409.1 | 497.1 | 497.1 |

Eudragit L100-55: Methacrylic acid copolymer, type C, Evonik Degussa GmbH
Kollicoat SR30D: polyvinylacetate 30% dispersion(polyvinylacetate 27%, polyvinylpyrrolidone 2.7%, sodium lauryl sulfate 0.3%), Basf AG

TABLE 5

| | Components | 30 | 31 | 32 | 33 | 34 | 35 | 36 | 37 | 38 |
|---|---|---|---|---|---|---|---|---|---|---|
| lag time Delayed-release layer | losartan potassium | 50.0 | 50.0 | 50.0 | 50.0 | 50.0 | 50.0 | 50.0 | 50.0 | 50.0 |
| | microcrystalline cellulose | 10 | 10 | 10 | 10 | 10 | 10 | 10 | 10 | 10 |
| | low-substituted hydroxypropyl cellulose LH11 | 20 | 20 | 20 | 20 | 20 | 20 | 20 | 20 | 20 |
| | crospovidone | 12 | 12 | 12 | 12 | 12 | 12 | 12 | 12 | 12 |
| | light anhydrous silicic acid | 3 | 3 | 3 | 3 | 3 | 3 | 3 | 3 | 3 |
| | povidone | 3 | 3 | 3 | 3 | 3 | 3 | 3 | 3 | 3 |
| | magnesium stearate | 2 | 2 | 2 | 2 | 2 | 2 | 2 | 2 | 2 |
| lag time delayed-release coating layer | Opadry 03B28796 | 2 | 2 | 2 | 2 | 2 | 2 | 2 | 2 | 2 |
| | Hypromellose acetate succinate | 10 | | | | | | | | |
| | Eudragit L100 | | 10 | | | | | | | |
| | Acryl-EZE | | | 10 | | | | | | |
| | Eudragit S100 | | | | 10 | | | | | |
| | Eudragit FS 30D | | | | | 10 | | | | |
| | Sureteric | | | | | | 10 | | | |
| | Cellulose acetate phthalate | | | | | | | 10 | | |
| | cellulose propionate phthalate | | | | | | | | 10 | |
| | shellac | | | | | | | | | 10 |
| Immediate release layer | Atorvastatin calcium anhydrate | 20.72 | 20.72 | 20.72 | 20.72 | 20.72 | 20.72 | 20.72 | 20.72 | 20.72 |
| | calcium carbonate | 66 | 66 | 66 | 66 | 66 | 66 | 66 | 66 | 66 |
| | Hydroxypropyl cellulose | 6 | 6 | 6 | 6 | 6 | 6 | 6 | 6 | 6 |

TABLE 5-continued

| | Components | Composition ratio(mg/tablet) Examples | | | | | | | | |
|---|---|---|---|---|---|---|---|---|---|---|
| | | 30 | 31 | 32 | 33 | 34 | 35 | 36 | 37 | 38 |
| | polysorbate 80 | 6 | 6 | 6 | 6 | 6 | 6 | 6 | 6 | 6 |
| | low-substituted hydroxypropyl cellulose (LH22) | 139 | 139 | 139 | 139 | 139 | 139 | 139 | 139 | 139 |
| | mannitol | 102.28 | 102.28 | 102.28 | 102.28 | 102.28 | 102.28 | 102.28 | 102.28 | 102.28 |
| | Crosslinked polyvinylpyrrolidone CL-SF | 35 | 35 | 35 | 35 | 35 | 35 | 35 | 35 | 35 |
| | Microcrystalline cellulose | 41.5 | 41.5 | 41.5 | 41.5 | 41.5 | 41.5 | 41.5 | 41.5 | 41.5 |
| | light anhydrous silicic acid | 3 | 3 | 3 | 3 | 3 | 3 | 3 | 3 | 3 |
| | low-substituted Hydroxypropyl cellulose (LH11) | 20 | 20 | 20 | 20 | 20 | 20 | 20 | 20 | 20 |
| | crospovidone | 32 | 32 | 32 | 32 | 32 | 32 | 32 | 32 | 32 |
| | Magnesium stearate | 3.5 | 3.5 | 3.5 | 3.5 | 3.5 | 3.5 | 3.5 | 3.5 | 3.5 |
| Coating layer | Opadry 03B28796 | 13 | 13 | 13 | 13 | 13 | 13 | 13 | 13 | 13 |
| | total | 600.0 | 600.0 | 600.0 | 600.0 | 600.0 | 600.0 | 600.0 | 600.0 | 600.0 |

Eudragit L100: Methacrylic acid copolymer, type A, Evonik Degussa GmbH
Acryl-EZE: Methacrylic acid copolymer, type C, Colorcon Inc.
Eudragit S100: Methacrylic acid copolymer, type B, Evonik Degussa GmbH
Eudragit FS 30D: poly(methyacrylate, methyl metacrylate, metacrylic acid 7:3:1 30% dispersion, Evonik Degussa GmbH
Sureteric: polyvinylacetatephthalate mixture, Colorcon Inc.

Test Example 1

Comparative Dissolution Profile Test

Comparative dissolution profile tests of the losartan/simvastatin two phase combination preparation, prepared in Example 1, and control drugs (Zocor® (simvastatin single tablet); Cozaar® (losartan single tablet)), were performed. The dissolution profile test of the simvastatin component was performed based on the United States Pharmacopoeia (USP30), and the dissolution profile test of the losartan component was performed for a total of 480 minutes, in which the dissolution medium was changed from artificial gastric juice to artificial intestinal juice starting from 120 minutes after the start of the test. The dissolution profile test of each component was performed in the following manner, and the test results are shown in FIG. 1.

As can be seen in FIG. 1, when the dissolution profile test was performed in the following conditions, the simvastatin component of the two-phase combination preparation of the present invention showed a dissolution profile substantially equal to that of control drug Zocor®, but the losartan component showed a very slow dissolution rate compared to that of control drug Cozaar®. For the losartan component, the dissolution rate of the losartan component up to 120 minutes corresponding to the artificial gastric juice zone was less than 10% for the losartan/simvastatin two-phase combination preparation of the present invention, but was about 60% for the control formulation. The dissolution rate of the losartan component in the subsequent artificial intestinal juice zone was 100% up to a total of 150 minutes for the control formulation, but was about 20% up to a total of 240 minutes for the losartan/simvastatin two-phase combination preparation of the present invention, suggesting that the dissolution rate of the losartan component for the inventive controlled-release tablet was much slower than that in the control formulation.

As described above, the early release of losartan in the losartan/simvastatin two-phase combination preparation of the present invention is much slower than simvastatin, unlike dissolution profiles obtained when the losartan single tablet and the simvastatin single tablet, as control drugs, are administered simultaneously. Thus, in the case of the inventive tablet, the time for metabolism-related enzyme cytochrome P450 to be reactivated after simvastatin is metabolized first in the liver can be sufficiently ensured.

[Simvastatin Test Method]

Dissolution profile test: performed based on the paragraph "simvastatin tablet" in the United States Pharmacopoeia (USP30).

Test method: paddle method, 50 rpm.

Dissolution medium: 900 ml of pH 7.0 buffer (composition=0.01M sodium dihydrogen phosphate solution containing 0.5 wt % of sodium lauryl sulfate as a surfactant).

Analysis method: UV/Vis spectrophotometry (detection wavelength=247-257 nm).

[Losartan Potassium Test Method]

Dissolution profile test: performed based on dissolution test method of general test methods in the Korean Pharmacopoeia, eighth edition.

Test method: paddle method, 50 rpm.

Dissolution media: 750 ml of 0.01M hydrochloric acid solution (artificial gastric juice); 1000 ml of pH 6.8 phosphate buffer solution (artificial intestinal juice).

Analysis method: UV/Vis spectrophotometry (detection wavelength=below 230 nm).

Test Example 2

Comparative Dissolution Profile Test

Figure 2:
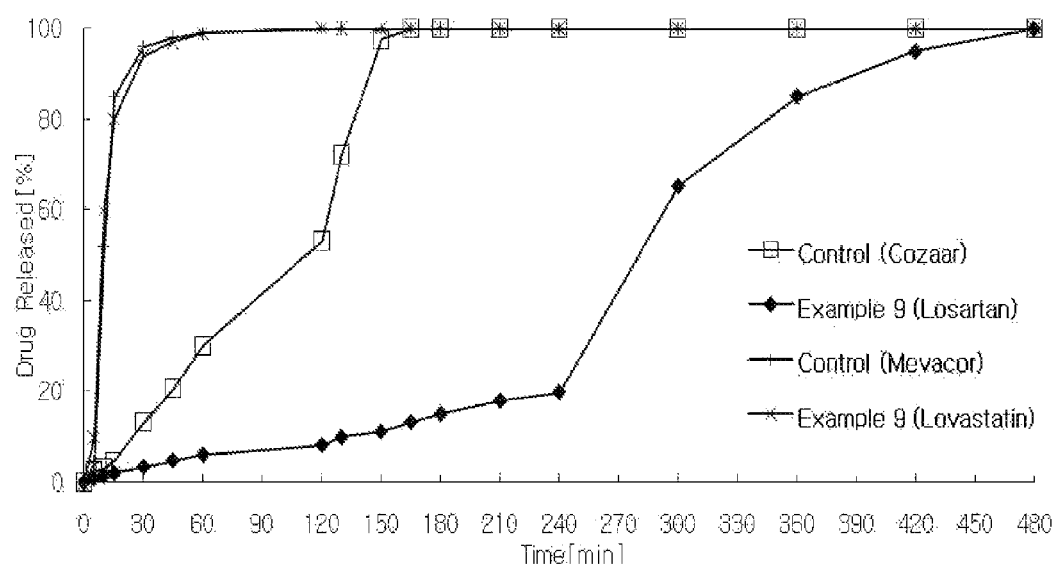
FIG. 2 is a diagram showing the comparative dissolution profiles of the combination preparation of losartan-lovastatin, prepared in Example 9, and the losartan and lovastatin components of single tablets, Cozaar® and Mevacor®, as control groups.

Comparative dissolution profile tests of the losartan/lovastatin two-phase combination preparation, prepared in Example 9, and control drugs (Mevacor® (lovastatin single tablet); Cozaar® (losartan single tablet)), were performed. The dissolution profile test of the lovastatin component was performed based on the United States Pharmacopoeia (USP30), and the dissolution profile test of the losartan component was performed up to a total of 480 minutes, in which the dissolution medium was changed from artificial gastric juice to artificial intestinal juice starting from 120 minutes after the start of the test. The dissolution profile test of each component was performed in the following manner, and the test results are shown in FIG. 2. The analysis of the losartan component was performed in the same manner as in Example 1.

As can be seen in FIG. 2, when the dissolution profile test was performed in the following conditions, the lovastatin component of the two-phase combination preparation of the present invention showed a dissolution profile substantially equal to that of the control drug Mevacor®, but the losartan component showed a very slow dissolution rate compared to that of the control drug Cozaar®. In the dissolution profile test results for the losartan component, the dissolution rate of the losartan component up to 120 minutes corresponding to the artificial gastric juice zone was less than 10% for the losartan/lovastatin two-phase combination preparation of the present invention, but was about 60% for the control drug. The dissolution rate of the losartan component in the subsequent artificial intestinal juice zone was 100% up to a total of 150 minutes for the control formulations, but was about 20% up to a total of 240 minutes for the losartan/lovastatin two-phase combination preparation of the present invention, suggesting that the dissolution rate of the losartan component in the inventive combination preparation was much slower than that of the control drug.

As described above, the early release of losartan in the losartan/lovastatin two-phase combination preparation of the present invention is much slower than simvastatin, unlike dissolution profiles obtained when the losartan single tablet and the lovastatin single tablet, as the control drugs, are administered simultaneously. Thus, in the case of the inventive tablet, the time for metabolism-related enzyme cytochrome P450 to be reactivated after lovastatin is metabolized first in the liver can be sufficiently ensured.

[Lovastatin Test Method]

Dissolution profile test: performed based on the paragraph "lovastatin tablet" in the United States Pharmacopoeia (USP30).

Test method: paddle method, 50 rpm.

Dissolution medium: 900 ml of pH=7.0 buffer (composition=0.01M sodium dihydrogen phosphate solution containing 2 wt % of sodium lauryl sulfate as a surfactant).

Analysis method: high-performance liquid chromatography.

Detection wavelength: 230 nm.

Mobile phase: acetonitrile: 0.02M sodium dihydrogen phosphate buffer (pH=4.0): methanol=5:3:1.

Column: stainless column (having an inner diameter of 4.6 cm and a length of 250 mm) packed with octadecyl silyl silica gel.

Flow rate: 1.5 mL/min.

Test Example 3

Comparative Dissolution Profile Test

Comparative dissolution profile tests of the combination preparations prepared in Examples 2-5 were performed. The dissolution profile test of each component was performed in the same manner as in Test Example 1, and the test results are shown in FIG. 3.

Figure 3:
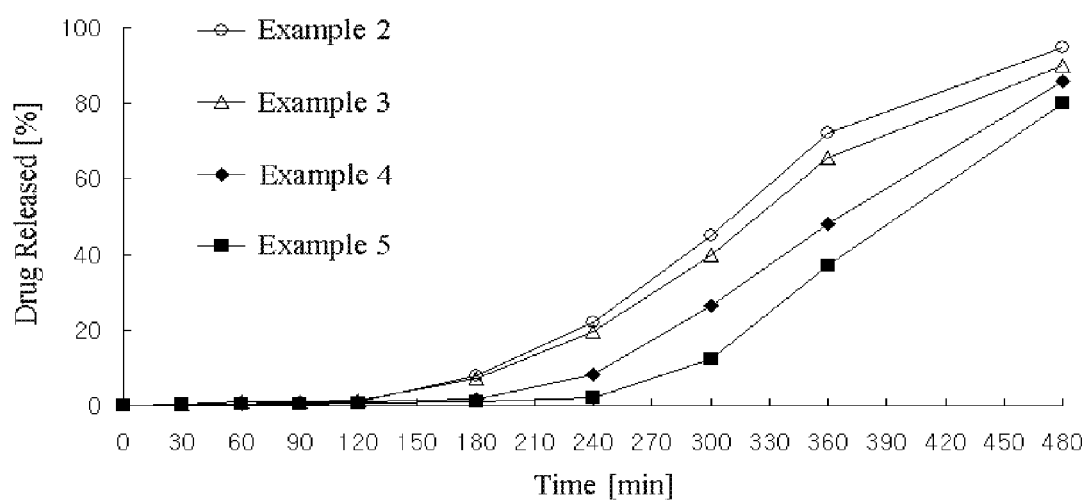
FIG. 3 is a graphic diagram showing the dissolution profiles of Examples 2-5.

As can be seen in FIG. 3, when the dissolution profile test was performed in the conditions of Test Example 1, the losartan component of the dry-coated tablet of the present invention showed a decrease in dissolution rate with an increase in the amount of ethylcellulose used. The formulations of Examples 2-5, coated with ethylcellulose, showed a losartan dissolution rate of less than 20% up to a total of 240 minutes.

As described above, the lag time of losartan in the inventive dry-coated tablet of losartan/simvastatin can be delayed up to the intended time by controlling the amount of ethylcellulose coated.

As described above, the early release of losartan in the losartan/simvastatin two-phase combination preparation of the present invention is much slower than simvastatin, unlike dissolution profiles obtained when the losartan single tablet and the simvastatin single tablet, as the control drugs, are administered simultaneously. Thus, in the case of the inventive tablet, the time for metabolism-related enzyme cytochrome P450 to be reactivated after simvastatin is metabolized first in the liver can be sufficiently ensured.

Test Example 4

Comparative Dissolution Profile Test

Figure 4:
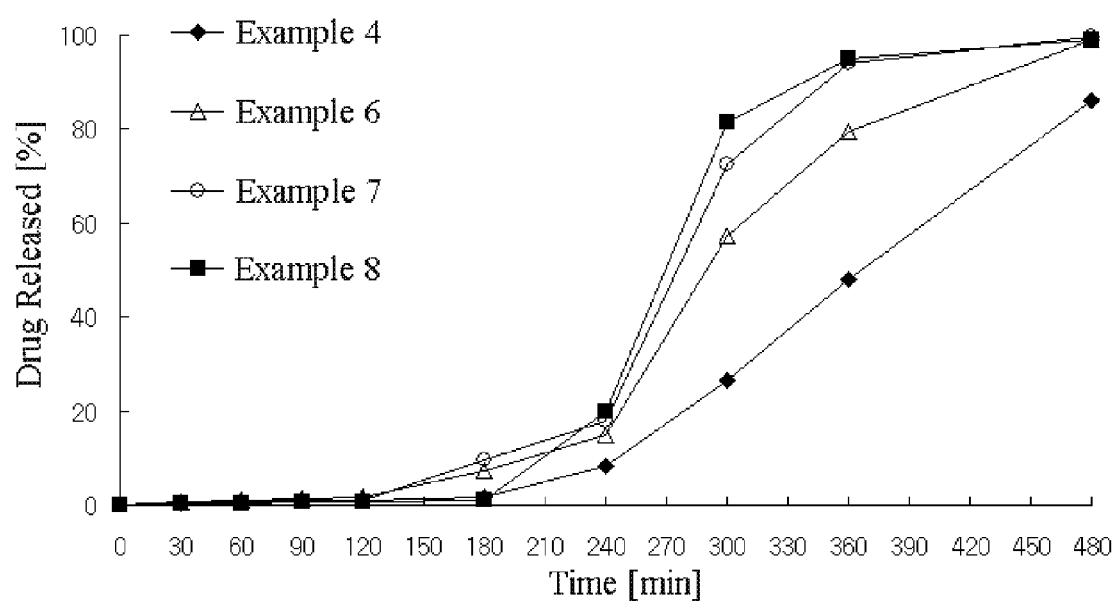
FIG. 4 is a graphic diagram showing the dissolution profiles of Examples 4 and 6-8.

Comparative dissolution profile tests of the combination preparation prepared in Examples 4 and 6-8 were performed. The dissolution profile test of each component was performed in the same manner as in Test Example 1, and the test results are shown in FIG. 4.

As can be seen in Table 4, in the results of the dissolution profile test performed in the conditions of Test Example 1, the losartan component of the dry-coated tablet of the present invention was rapidly released after an intended lag time, when the delayed-release layer coated with ethyl cellulose contained crosslinked polyvinylpyrrolidone (copovidone). The dissolution rate of the losartan component was less than 20% up to a total of 240 minutes, and the losartan component was rapidly released with an increase in the amount of crosslinked polyvinylpyrrolidone used.

As described above, the losartan component of the inventive dry-coated tablet of losartan/simvastatin can be more rapidly released after an intended lag time by controlling the amount of crosslinked polyvinylpyrrolidone used in the delayed-release layer.

As described above, the early release of losartan in the losartan/simvastatin two-phase combination preparation of the present invention is much slower than simvastatin, unlike dissolution profiles obtained when the losartan single tablet and the simvastatin single tablet, as the control drugs, are administered simultaneously. Thus, in the case of the inventive tablet, the time for metabolism-related enzyme cytochrome P450 to be reactivated after simvastatin is metabolized first in the liver can be sufficiently ensured.

Test Example 5

Comparative Dissolution Profile Test

Figure 5:
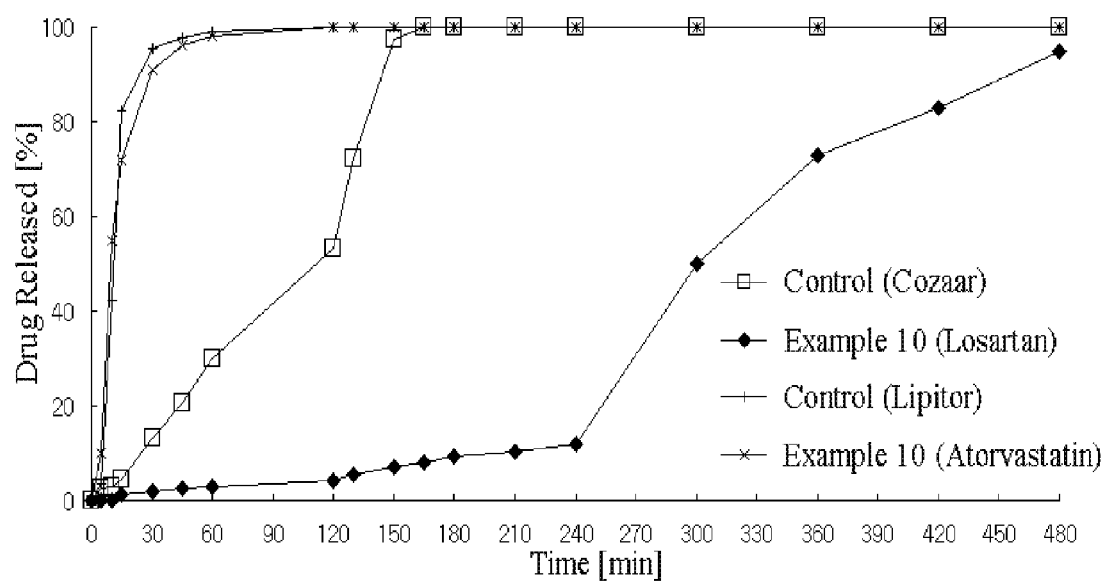
FIG. 5 is a diagram showing the comparative dissolution profiles of the combination preparation of losartan-atorvastatin, prepared in Example 10, and the losartan and atorvastatin components of single tablets, Cozaar® and Lipitor®, as control groups.

Comparative dissolution profile tests of the losartan/atorvastatin two-phase combination preparation, prepared in Example 10, and control drugs (Lipitor® (atorvastatin single tablet); Cozaar® (losartan single tablet), were performed. The dissolution profile test of atorvastatin was performed based on the dissolution test method of general test methods contained in the Korean Pharmacopoeia, eighth edition, and the dissolution profile test of the losartan component was performed for a total of 480 minutes, in which the dissolution medium was changed from artificial gastric juice to artificial intestinal juice starting from 120 minutes after the start of the test. The dissolution profile test of each component was performed in the following manner, and the test results are shown in FIG. 5. The analysis of the losartan component was performed in the same manner as Example 1.

As can be seen in FIG. 5, when the dissolution profile test was performed in the following conditions, the atorvastatin component of the two-phase combination preparation of the present invention showed a dissolution profile substantially equal to that of the control drug Lipitor®, but the losartan component showed a very slow dissolution rate compared to that of the control drug Cozaar®. In the dissolution profile test results for the losartan component, the dissolution rate of the losartan component up to 120 minutes corresponding to the artificial gastric juice zone was less than 10% for the losartan/atorvastatin two-phase combination preparation of the present invention, but was about 60% for the control drug. The dissolution rate of the losartan component in the subsequent artificial intestinal juice zone was 100% up to a total of 150 minutes for the control formulations, but was about 20% up to a total of 240 minutes for the losartan/atorvastatin two-phase combination preparation of the present invention, suggesting that the dissolution rate of the losartan component in the inventive combination preparation was much slower than that of the control drug.

As described above, the early release of losartan in the losartan/atorastatin two-phase combination preparation of the present invention is much slower than atorastatin, unlike dissolution profiles obtained when the losartan single tablet and the atorvastatin single tablet, as the control drugs, are administered simultaneously. Thus, in the case of the inventive tablet, the time for metabolism-related enzyme cytochrome P450 to be reactivated after atorvastatin is metabolized first in the liver can be sufficiently ensured.

[Atorvastatin Test Method]

Dissolution profile test: performed based on dissolution test method of general test methods in the Korean Pharmacopoeia, eighth edition.

Test method: paddle method, 50 rpm.

Dissolution medium: 900 ml of pH 7.0 buffer (composition=0.01M sodium dihydrogen phosphate solution containing 2 wt % of sodium lauryl sulfate as a surfactant).

Analysis method: high-performance liquid chromatography

Detection wavelength: 247 nm

Mobile phase: 0.02M sodium dihydrogen phosphate buffer (pH=4.0): methanol=67:33.

Column: Stainless column (having an inner diameter of 4.6 cm and a length of 250 mm) packed with octadecyl silyl silica gel.

Flow rate: 1.5 mL/min.

Test Example 6

Comparative Dissolution Profile Test

Comparative dissolution profile tests of the losartan/simvastatin two-phase combination lag time delayed-release tablets, prepared in Examples 14 and 19, and control drugs (Zocor® (simvastatin single tablet); Cozaar® (losartan single tablet)), were performed. The dissolution profile test of the simvastatin component was performed based on the United States Pharmacopoeia (USP30), and the dissolution profile test of the losartan component was performed for a total of 480 minutes, in which the dissolution medium was changed from artificial gastric juice to artificial intestinal juice starting from 120 minutes after the start of the test. The dissolution profile test of each component was performed in the same manner as in Test Example 1, and the test results are shown in FIG. 6.

Figure 6:
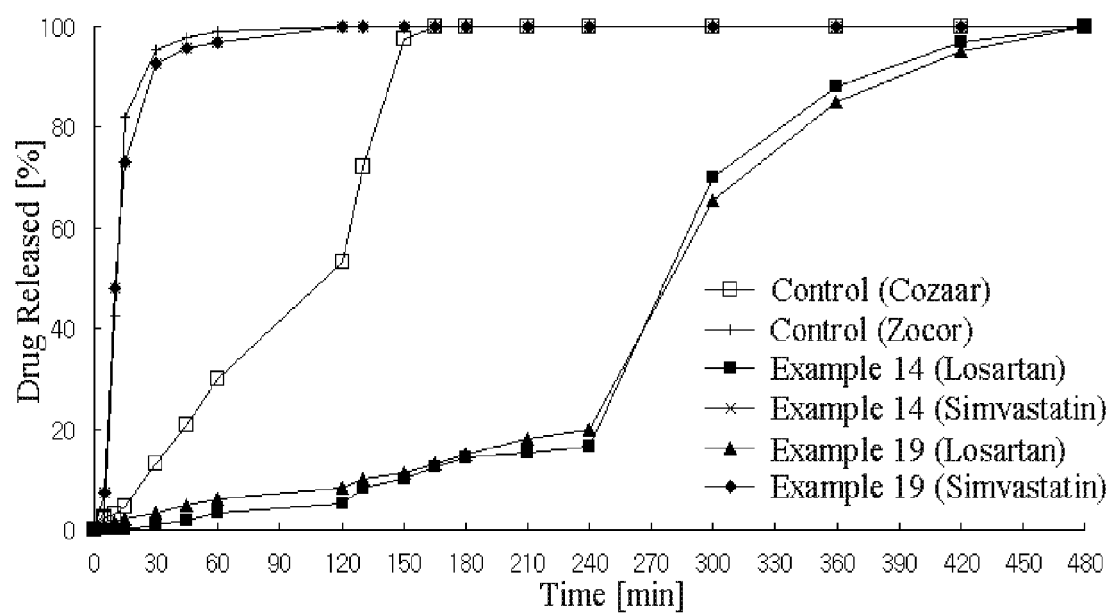
FIG. 6 is a diagram showing the comparative dissolution profiles of the combination preparation of losartan-simvastatin, prepared in each of Examples 14 and 19, and the losartan and simvastatin components of single tablets, Cozaar® and Zocor®, as control groups.

As can be seen in FIG. 6, when the dissolution profile test was performed in the conditions of Test Example 1, the simvastatin component of the two-phase combination preparation of the present invention showed a dissolution profile substantially equal to that of the control drug Zocor®, but the losartan component showed a very slow dissolution rate compared to that of the control drug Cozaar®. In the dissolution profile test results for the losartan component, the dissolution rate of the losartan component up to 120 minutes corresponding to the artificial gastric juice zone was less than 10% for the losartan/simvastatin two-phase combination preparation of the present invention, but was about 60% for the control formulation. The dissolution rate of the losartan component in the subsequent artificial intestinal juice zone was 100% up to a total of 150 minutes for the control formulation, but was about 20% up to a total of 240 minutes for the losartan/simvastatin two-phase combination lag time delayed-release tablet of the present invention, suggesting that the dissolution rate of the losartan component in the inventive lag time delayed-release tablet was much slower than that of the control formulation.

As described above, the early release of losartan in the losartan/simvastatin two-phase combination preparation of the present invention is much slower than simvastatin, unlike dissolution profiles obtained when the losartan single tablet and the simvastatin single tablet, as control drugs, are administered simultaneously. Thus, in the case of the inventive tablet, the time for metabolism-related enzyme cytochrome P450 to be reactivated after simvastatin is metabolized first in the liver can be sufficiently ensured.

Test Example 7

Comparative Dissolution Profile Test

Figure 7:
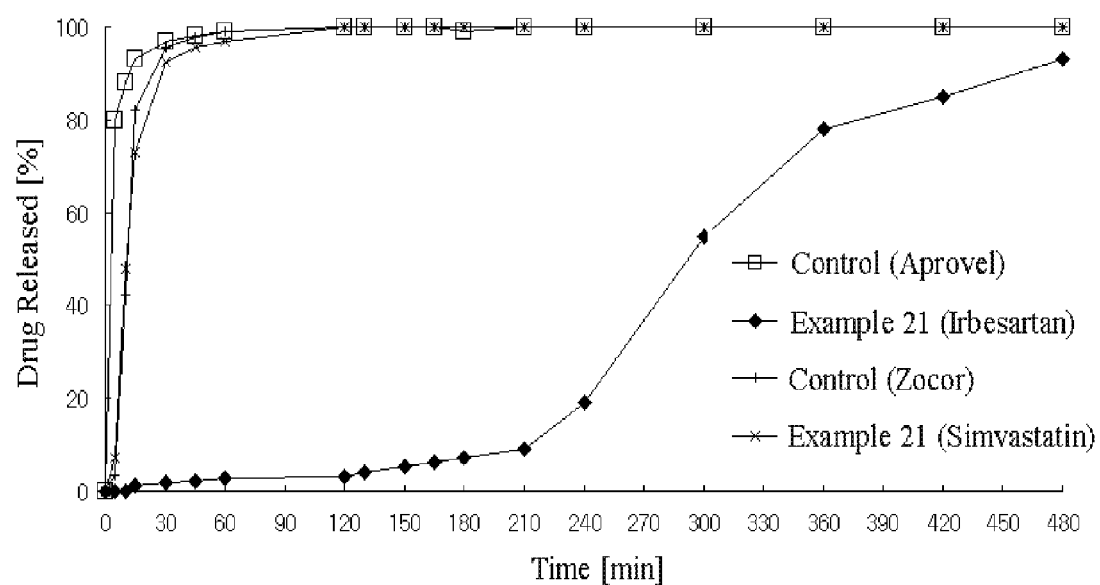
FIG. 7 is a diagram showing the comparative dissolution profiles of the combination preparation of irbesartan/simvastatin, prepared in each of Example 21, and the irbesartan and simvastatin components of single tablets, Aprovel® and Zocor®, as control groups.

Comparative dissolution profile tests of the Irbesartan/simvastatin two-phase combination preparation, prepared in Example 21, and control drugs (Zocor® (simvastatin single tablet); Aprovel® (Irbesartan single tablet)), were performed. The dissolution profile test of the simvastatin component was performed based on the United States Pharmacopoeia (USP30), and the dissolution profile test of the irbesartan component was performed for a total of 480 minutes, in which the dissolution medium was changed from artificial gastric juice to artificial intestinal juice starting from 120 minutes after the start of the test. The dissolution profile test of each component was performed in the following manner, and the test results are shown in FIG. 7. The analysis of the simvastatin component was performed in the same manner as in Test Example 1.

As can be seen in FIG. 7, when the dissolution profile test was performed in the following conditions, the simvastatin component of the two-phase combination preparation of the present invention showed a dissolution profile substantially equal to that of the control drug Zocor®, but the irbesartan component showed a very slow dissolution rate compared to that of the control drug Aprovel®. In the dissolution profile test results for the irbesartan component, the dissolution rate of the irbesartan component up to 120 minutes corresponding to the artificial gastric juice zone was less than 10% for the irbesartan/simvastatin two-phase combination preparation of the present invention, but was about 100% for the control formulation. The dissolution rate of the irbesartan component in the subsequent artificial intestinal juice zone was 100% up to a total of 150 minutes for the control formulation, but was about 20% up to a total of 240 minutes for the irbesartan/simvastatin two-phase combination preparation of the present invention, suggesting that the dissolution rate of the irbesartan component in the inventive combination preparation was much slower than that of the control formulation.

As described above, the early release of irbesartan in the irbesartan/simvastatin two-phase combination preparation of the present invention is much slower than simvastatin, unlike dissolution profiles obtained when the irbesartan single tablet and the simvastatin single tablet, as the control drugs, are administered simultaneously. Thus, in the case of the inventive combination preparation, the time for metabolism-related enzyme cytochrome P450 to be reactivated after simvastatin is metabolized first in the liver can be sufficiently ensured.

[Irbesartan Test Method]
Dissolution test: performed based on dissolution test method of general test methods in the Korean Pharmacopoeia, eighth edition.
Test method: paddle method, 50 rpm.
Dissolution media: 750 ml of 0.01M hydrochloric acid solution (artificial gastric juice); 1000 ml of pH 6.8 phosphate buffer solution (artificial intestinal juice).
Analysis method: high-performance liquid chromatography
Detection wavelength: 220 nm.
Mobile phase: acetonitrile: phosphate buffer (pH=3.7)=33:67
Column: stainless column (having an inner diameter of 4.0 cm and a length of 250 mm) packed with octadecyl silyl silica gel.
Flow rate: 1.0 mL/min.

Test Example 8

Comparative Dissolution Profile Test

Figure 8:
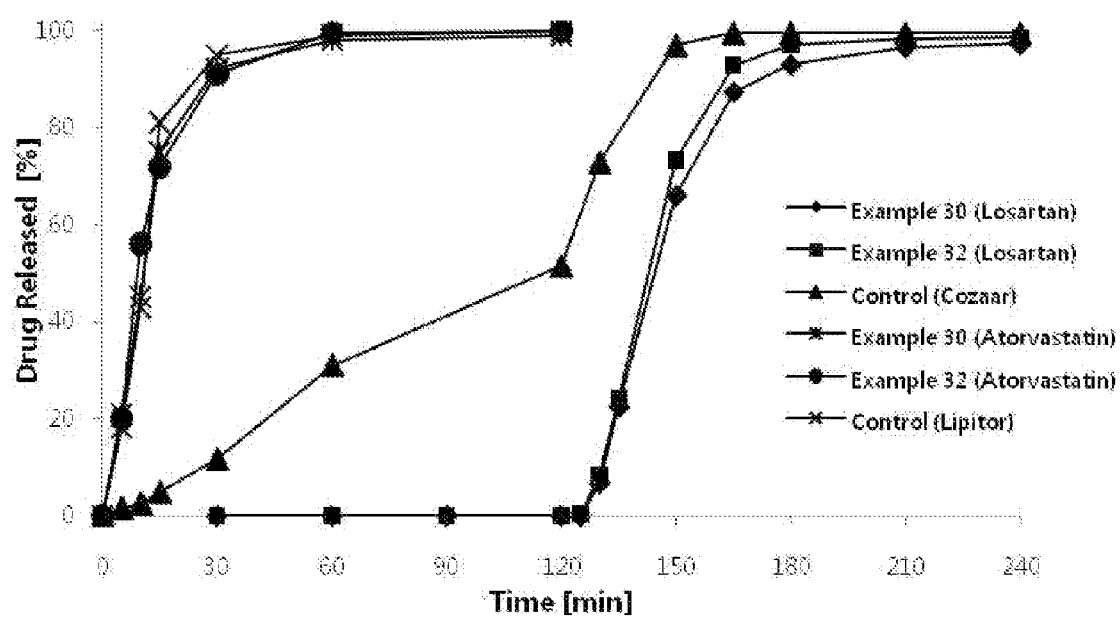
FIG. 8 is a graphic diagram shows the clinical study results of Test Example 8 and indicates the dissolution profile of the combination preparation.

Comparative dissolution profile tests of the losartan/atorvastatin two-phase combination preparations, prepared in Examples 30 and 32, and control drugs (Lipitor® (atorvastatin single tablet); Cozaar® (losartan single tablet), were performed. The dissolution profile test of atorvastatin was performed based on the dissolution test method of general test methods contained in the Korean Pharmacopoeia, eighth edition, and the dissolution profile test of the losartan component was performed for a total of 240 minutes, in which the dissolution medium was changed from artificial gastric juice to artificial intestinal juice starting from 120 minutes after the start of the test. The dissolution profile test of each component was performed in the following manner, and the test results are shown in FIG. 8. The analysis of the losartan component was performed in the same manner as in Example 1.

As can be seen in FIG. 8, when the dissolution profile test was performed in the following conditions, the atorvastatin component of the two-phase combination preparation of the present invention showed a dissolution profile substantially equal to that of the control drug Lipitor®, but release of the losartan component was delayed up to about 2 hours compared to that of the control drug Cozaar®. In the dissolution profile test results for the losartan component, the losartan component in the losartan/atorvastatin two-phase combination preparation of the present invention was not dissolved up to 120 minutes corresponding to the artificial gastric juice zone, but the losartan component in the control drug shows the dissolution rate of 50% or more. Further, it can be confirmed that the combination preparation of Examples 30 and 32 showed the same dissolution pattern even though the release-controlling materials were different in formulation.

As described above, the early release of losartan in the losartan/atorastatin two-phase combination preparation of the present invention is much slower than atorvastatin, unlike dissolution profiles obtained when the losartan single tablet and the atorvastatin single tablet, as the control drugs, are administered simultaneously. Thus, in the case of the inventive tablet, the time for metabolism-related enzyme cytochrome P450 to be reactivated after atorvastatin is metabolized first in the liver can be sufficiently ensured.

[Atorvastatin Test Method]
Dissolution profile test: performed based on dissolution test method of general test methods in the Korean Pharmacopoeia, eighth edition.
Test method: paddle method, 50 rpm.
Dissolution medium: 900 ml of pH 7.0 buffer (composition=0.01M sodium dihydrogen phosphate solution containing 2 wt % of sodium lauryl sulfate as surfactant).
Analysis method: high-performance liquid chromatography
Detection wavelength: 247 nm
Mobile phase: 0.02M sodium dihydrogen phosphate buffer (pH=4.0): methanol=67:33.
Column: Stainless column (having an inner diameter of 4.6 cm and a length of 250 mm) packed with octadecyl silyl silica gel.
Flow rate: 1.5 mL/min.

Test Example 9

Animal Study

In this Test Example, an animal study was performed as described in Table 6 below in order to confirm the effect of the inventive composition. Specifically, in a control group, commercially available control drugs (Zocor® tablet, MSD (simvastatin single tablet) and Cozaar® tablet, MSD (losartan single tablet)) were simultaneously administered. In a test group, the drugs were administered at different times, such that the release times of the drugs were the same as in the composition provided in the Examples of the present invention, and thus the effects of the drugs were the same as those of the inventive composition.

Also, this animal study was designed such that the administration time showing the maximum antihypertensive effect could be confirmed.

TABLE 6

| | |
|---|---|
| Title | Animal study for the comparison of antihypertensive effect between the simultaneous administration of losartan and simvastatin and the administration of the drugs at different times in spontaneously hypertensive rats (SHR) rats. |
| Object | To comparatively evaluate steady-state pharmacokinetic properties, the antihypertensive effect and safety of simultaneous administration of losartan and simvastatin and the administration of the drugs at different times and to comparatively evaluate pharmacokinetic properties, antihypertensive effect and safety of administration times. |

TABLE 6-continued

| | |
|---|---|
| Test subjects | Twenty-five 8-week-old male SHR rats grouped into five groups, each consisting of five animals, and four 9-week-old male Wistar Kyoto rats. |
| Test design | The design of this test is as follows. As test dugs, losartan and simvastatin were used. A total of 29 animals were grouped into the following six groups, each consisting of 5 animals: a saline-administered WKY rat group as a control group; a saline-administered SHR rat group as a screening group; a test group administered losartan and simvastatin simultaneously in the morning (SM group) (dark conditions); a test group administered losartan and simvastatin simultaneously in the evening (SN group) (light conditions); a test group administered losartan and simvastatin at different times in the morning (DM group) (dark conditions); a test group administered losartan and simvastatin at different times in the evening (DN group) (light conditions) (three big groups: a control group, a screening group and a test group). The drugs were administered for 5 days once a day. Because this study is an animal study using rats as test models, the test was performed in light conditions and dark conditions. The administration time applied in the animal study is conversely applied to humans, because the biorhythm of rats is opposite to the biorhythm of humans. |
| Evaluation method | Evaluation of effects Comparison of changes in systolic blood pressure, diastolic blood pressure, mean blood pressure and pulse rate, were measured with an automatic blood pressure meter, among the groups administered the drugs simultaneously in the morning and in evening, and the groups administered the drugs at different times in the morning and in evening. |

| | Group name | Administered drugs and method (administrated on concentration of 5 ml/kg) | Animal number |
|---|---|---|---|
| Test groups | Normal (WKY rats, saline) | Administered saline hourly | 4 |
| | Vehicle (saline) | Administered saline hourly | 5 |
| | Administered with losartan and simvastatin simultaneously in the morning (SM group) (dark conditions) | Administered losartan and simvastatin simultaneously at 9:30 a.m. | 5 |
| | Administered with losartan and simvastatin simultaneously in the evening (SN group) (light conditions) | Administered losartan and simvastatin simultaneously at 7 p.m. | 5 |
| | Administered with losartan and simvastatin at different times in the morning (DM group) (dark conditions) | Administered losartan at 9:30 a.m.; Administered simvastatin at 1:30 p.m. | 5 |
| | Administered with losartan and simvastatin at different times in the evening (DN group) (light conditions) | Administered losartan at 7 p.m.; Administered simvastatin at 11 p.m. | 5 |

Figure 9:
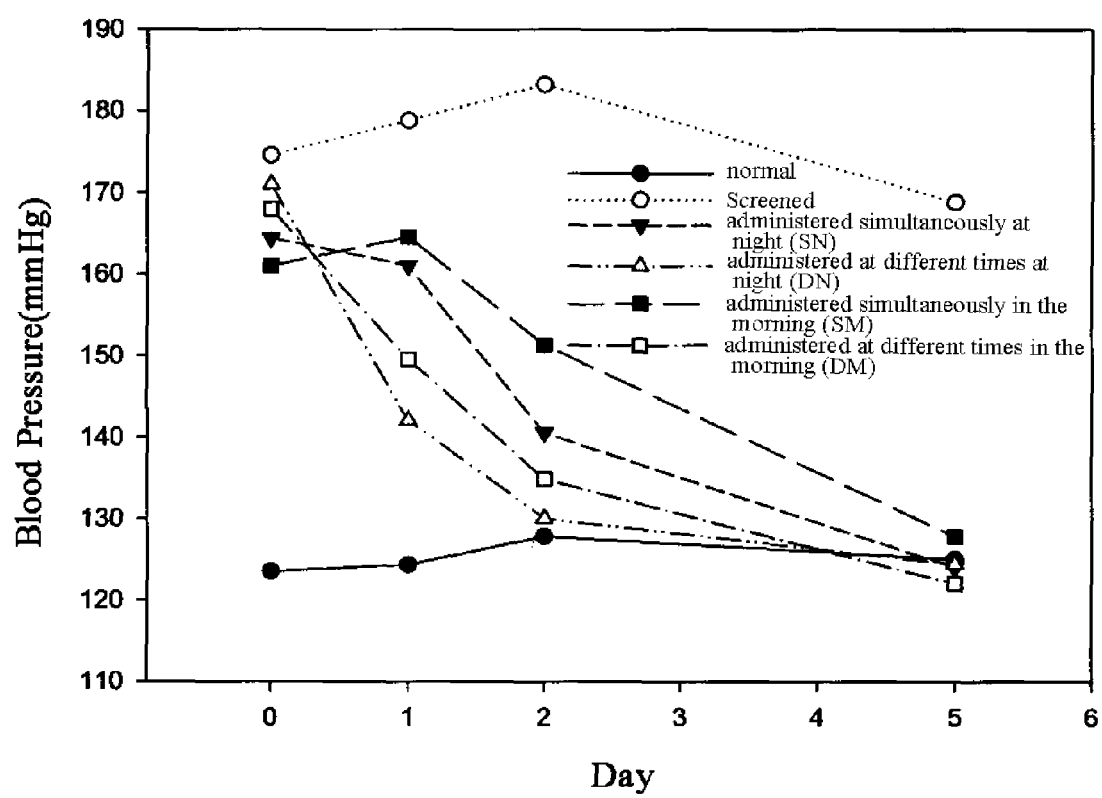
FIG. 9 is a graphic diagram shows the clinical study results of Test Example 9 and indicates the systolic blood pressures between dosage methods.
Figure 10:
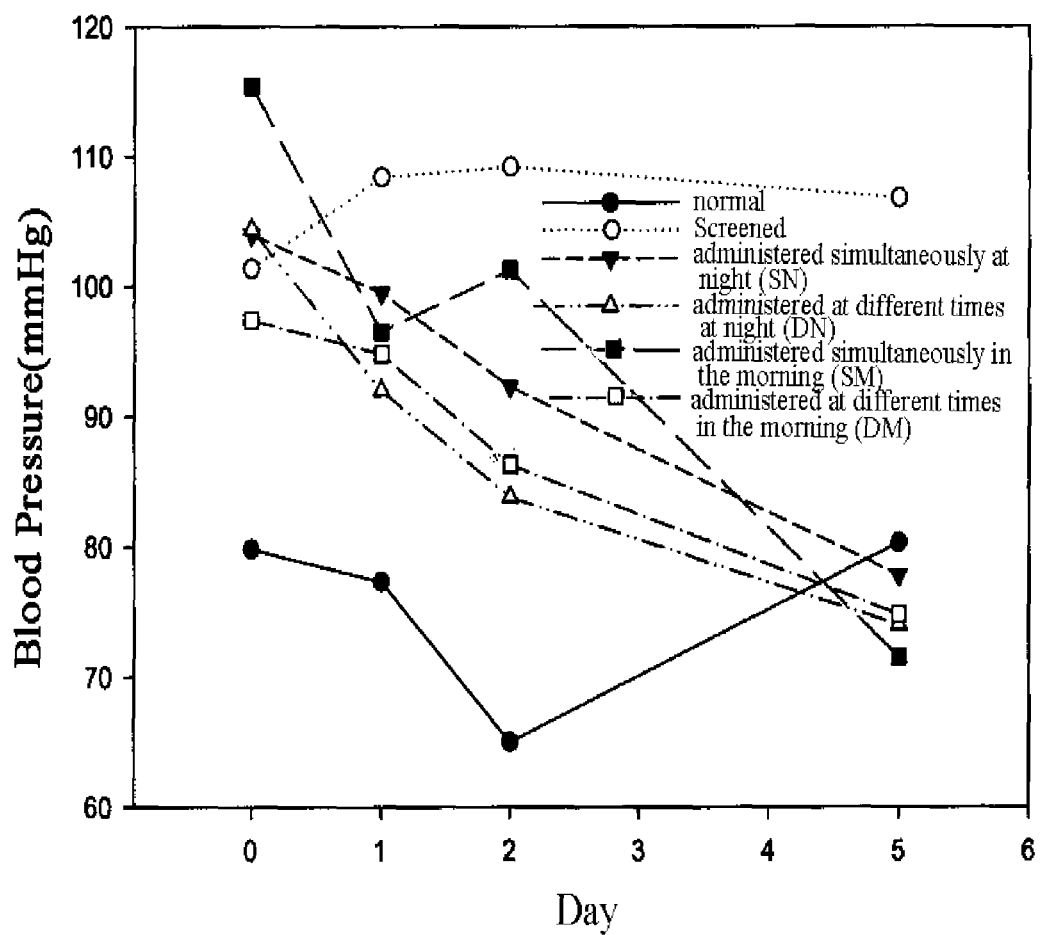
FIG. 10 is a graphic diagram shows the clinical study results of Test Example 9 and indicates the diastolic blood pressures between dosage methods.
Figure 11:
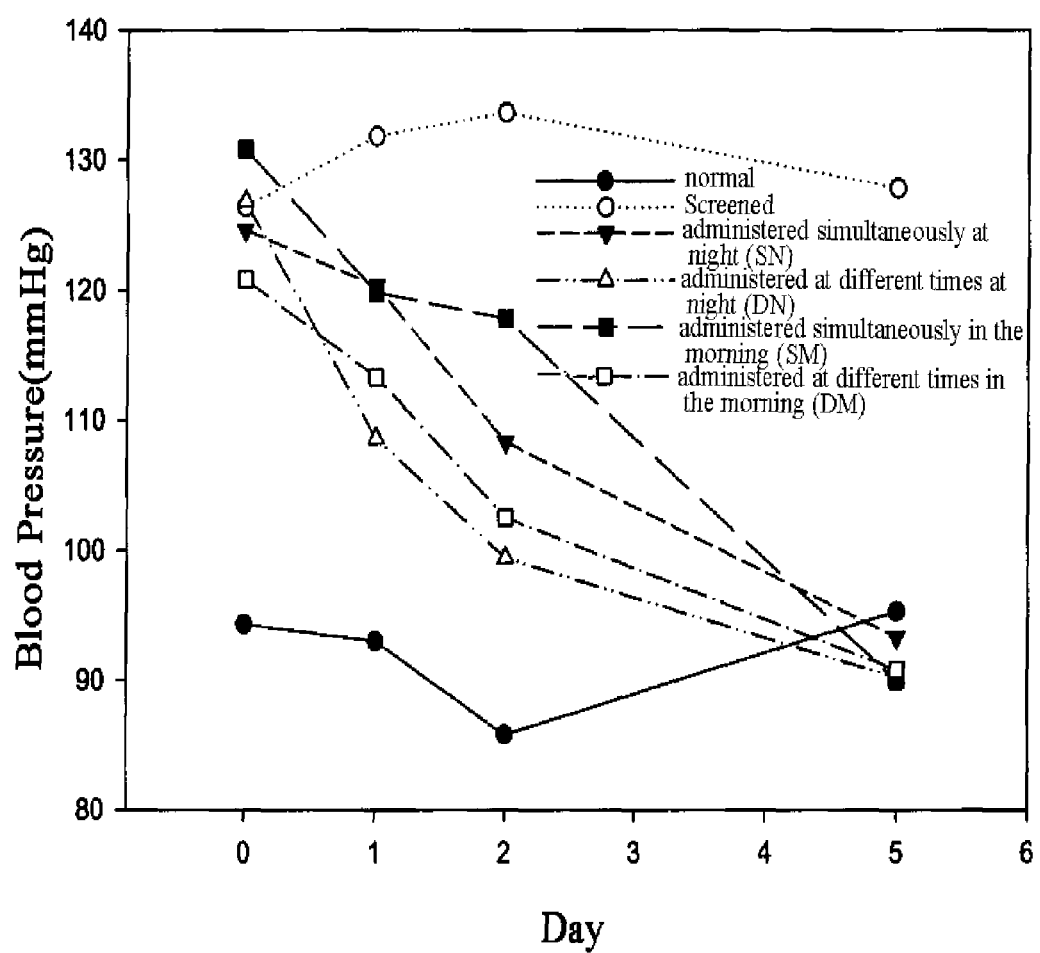
FIG. 11 is a graphic diagram shows the clinical study results of Test Example 9 and indicates the mean blood pressures between dosage methods.

Pharmacokinetic/pharmacodynamic results of the clinical animal study, performed in this Test Example, are shown in Table 7 below and FIGS. 9 to 11.

TABLE 7

Results of the comparative animal study between the administration at different times and simultaneous administration

| 1 | Items | WKY rats | SHR rats | SHR rats | SHR rats | SHR rats | SHR rats |
|---|---|---|---|---|---|---|---|
| 2 | Groups | Normal group | Triple-distilled water | Group administered simultaneously in the morning (dark conditions) | Group administered simultaneously in the evening (light conditions) | Group administered at different times in the morning (dark conditions) | Group administered at different times in the evening (light conditions) |
| 3 | Animal number | 4 | 5 | 5 | 5 | 5 | 5 |
| | | | | State of animals at 20 hours after 5-day administration | | | |
| 4 | systolic blood pressure (mmHg) | 125.0 ± 5.5 | 168.8. ± 8.3 | 127.8 ± 10.5 | 124.0 ± 8.0 | 122.0 ± 9.5 | 124.4 ± 1.7 |
| 5 | diastolic blood pressure (mmHg) | 80.3 ± 15.5 | 106.8 ± 22.8 | 71.5 ± 17.3 | 77.8 ± 14.1 | 74.8 ± 11.0 | 74.0 ± 13.1 |

TABLE 7-continued

Results of the comparative animal study between the administration
at different times and simultaneous administration

| | | | | | | |
|---|---|---|---|---|---|---|
| 6 | Mean blood pressure (mmHg) | 95. ± 10.6 | 127.8 ± 13.9 | 90.0 ± 8.4 | 93.3 ± 8.4 | 90.8 ± 9.2 | 90.2 ± 9.8 |
| 7 | Pulse rate (rate/min) | 457.0 ± 55.0 | 439.0 ± 18.6 | 460.8 ± 74.3 | 498.8 ± 45.0 | 465.5 ± 30.4 | 463.6 ± 58.6 |

<This animal study was performed on rats as test models under light conditions and dark conditions. The administration time applied in the animal study is conversely applied to humans, because the biorhythm of rats is opposite to the biorhythm of humans.>

1. In blood pressure reducing effects, systolic blood pressure and diastolic blood pressure showed low values at day 5 compared to the screening group.

2. The blood pressure reducing effects are shown in FIGS. 9 to 11. It was observed that the group administered at different times in the evening (light conditions) was most excellent for the blood pressure reducing effect among the four groups.

Thus, it can be seen that, unlike the conventional group administered simultaneously, the composition of the present invention has the optimal blood pressure reducing effect during a time period from the morning to midday of the day following the administration thereof, when the average blood pressure reaches a peak.

It can be seen that, in the case of administration at different times, like the case of the novel combination preparation of the present invention comprising the angiotensin-II-receptor blocker and the HMG-CoA reductase inhibitor, the angiotensin-II-receptor blocker and the HMG-CoA reductase inhibitor, administered to reduce blood pressure, show an optimal antihypertensive effect compared to when single formulations of each of the angiotensin-II-receptor blocker and the HMG-CoA reductase inhibitor are simultaneously administered.

Meanwhile, Table 8 below shows the results of the measurement of blood pressure and pulse rate in the group administered with losartan and simvastatin simultaneously and the test group administered at different times in the morning according to the present invention. As can be seen in Table 8, with respect to the blood pressure reducing effects of losartan and simvastatin, the test group administered at different times according to the present invention showed an increase of 0.3% in mean sitting systolic blood pressure compared to the group administered simultaneously, but the increase was not significant. Also, the inventive test group showed an increase of 4.8% in mean sitting diastolic blood pressure reducing effect, an increase of 3.3% in mean blood pressure reducing effect and an increase of 7.1% in pulse rate reducing effect, compared to the group administered simultaneously. Thus, the inventive test group showed a significant increase in the overall blood pressure-reducing effect.

TABLE 8

| Groups | Blood pressure (systolic) (mmHg) | Blood pressure (diastolic) (mmHg) | Blood pressure (mean) (mmHg) | Pulse rate (per min) |
|---|---|---|---|---|
| Normal group | 125.0 ± 5.5 | 80.3 ± 15.5 | 95. ± 10.6 | 457.0 ± 55.0 |
| Screening group | 168.8 ± 8.3 | 106.8 ± 22.8 | 127.8 ± 13.9 | 439.0 ± 18.6 |
| Administered at different times in the evening | 124.4 ± 1.7 | 74.0 ± 13.1 | 90.2 ± 9.8 | 463.6 ± 58.6 |
| Administered simultaneously in the evening | 124.0 ± 8.0 | 77.8 ± 14.1 | 93.3 ± 8.4 | 498.8 ± 45.0 |
| Difference in blood pressure drop between simultaneous administration and administration at different times | −0.3% | +4.8% | +3.3% | +7.1% |

<This animal study was performed on rats as test models under light/dark conditions. The administration time applied in the animal study is conversely applied to humans, because the biorhythm of rats is opposite to the biorhythm of humans.>

Accordingly, through the delayed release of losartan, administered after 4 hours as intended in the present invention in order to reduce blood pressure, it was demonstrated that the group administered with the drugs at different times had an excellent blood pressure-reducing effect compared to the group administered with the drugs simultaneously.

Test Example 10

Preliminary Clinical Study

The preliminary clinical study was performed as described in Table 9 below in order to confirm the effect of the inventive combination preparation. Specifically, in control groups, commercially available control "Zocor® tablet" (20 mg simvastatin; MSD) was administered alone, and "Zocor® tablet" and "Cozaar®tablet" (50 mg losartan potassium; MSD) were administered simultaneously. In a test group, "Zocor® tablet" and "Cozaar® tablet" were administered at different times, such that the release times of the drugs were the same as in the combination preparation provided in Example of the present invention.

TABLE 9

| | |
|---|---|
| Title | A multi institutional clinical study compared the pharmacokinetic properties, effects and safety of administration of losartan and simvastatin simultaneously and administration of losartan and simvastatin at different times in hypertensive and hyperlipidemia patients (study research, investigator-initiated trial) |
| Object | To comparatively evaluate pharmacokinetic properties, effects and safety between a group administered with Zocor ® and Cozaar ® simultaneously and a group administered with the drugs at different times after administration once a day for 6 weeks (42 days) in hypertension and hyperlipidemia patients. |
| Subjects | Seventeen 30~60-year-old patients having hypertension and hyperlipidemia; 8 patients administered with the drugs simultaneously and 9 patients administered with the drugs at different times. |
| Design | This test was designed as follows:<br>2-open labeled, and single dose.<br>Test drug 1: 50 mg Cozaar ® (one tablet)<br>Test drug 2: 20 mg Zocor ® (one tablet).<br>Group A: administered Zocor ® and Cozaar ® simultaneously in the evening.<br>Group B: administered Zocor ® and Cozaar ® at different times in the evening.<br>The drugs were administered for 6 weeks (42 days), and a comparison between the two groups was performed. |
| Efficacy and Safety | 1. Efficacy evaluation<br>Primary endpoint: comparison of changes (between before treatment and end of study) in mean systolic blood pressure and LDL-C, between two groups, i.e., the group administered simultaneously and the group administered at different times.<br>Second endpoints: comparison of changes (between before treatment and end of study) in mean sitting diastolic pressures and pulse pressure, lipid profiles (total cholesterol (mg/dl), LDL-cholesterol (mg/dl), HDL-cholesterol (mg/dl), triglyceride (mg/dl), other risk factors (Apo B, HDL-C/LDL-C)), and CV risk group, between the two groups.<br>2. Safety evaluation<br>Physical examination, vital sign, adverse events, ECG etc. |

| Group name | Administered drugs and method | Number of patients |
|---|---|---|
| Test groups | Group administered at different times in the evening | Administered 20 mg Zocor ® at 7 p.m., and after 4 hours, administered 50 mg Cozaar ® at 11 p.m. | 9 |
| | Group administered simultaneously in the evening | Administered with 50 mg Cozaar ® and 20 mg Zocor ® simultaneously at 7 p.m. | 8 |

This study supports the effects of the present invention and was performed according to ICH-GCP and KGCP except the study was performed for a small number of patient groups compared to guidelines of ICH-GCP and KGCP. Lipids measured at 42 days (fasted state) after the start of administration in this clinical study are shown in Table 10 below.

TABLE 10

| Lipids | Group A (administered simultaneously; 8 patients) | | | Group B (administered at different times; 9 patients) | | | Results |
|---|---|---|---|---|---|---|---|
| | Screening | D 42 | Change(%) | Screening | D 42 | Change(%) | |
| Total cholesterol (120-230 mg/dl) | 208.6 | 151.3 | −57.4 (27.5%) | 251.1 | 172.3 | −78.8 (31.4%) | Group B was better. |
| LDL-cholesterol (0-120 mg/dl) | 139.6 | 82.6 | −57.00 (40.8%) | 174.2 | 95.1 | −79.1 (45.4%) | Group B was better. |
| HDL/LDL | 0.302 | 0.519 | 0.217 (71.9%) | 0.312 | 0.538 | 0.226 (72.4%) | The two groups showed a significant increase |
| Triglyceride (40-150) | 177.5 | 175.9 | −1.6 (0.9%) | 172.4 | 161.4 | −11.0 (6.4%) | Group B was better. |

Blood pressure, pulse rate and pulse pressure, measured at 41 days after the start of administration in this clinical test, are shown in Table 11 below.

TABLE 11

| | Group A (administered simultaneously; 8 patients) | | | Group B (administered at different times; 9 patients) | | | Results |
|---|---|---|---|---|---|---|---|
| | Screening | D 41 | Change | Screening | D 41 | Change | |
| BP (SYS) | 148.3 | 141.3 | −7.0 (4.7%) | 145.2 | 132.4 | −12.7 (8.7%) | Group B was better |
| BP (DYS) | 99.4 | 90.0 | −9.4 (9.5%) | 94.8 | 80.9 | −13.9 (14.7) | Group B was better |
| Pulse pressure | 53.1 | 51.3 | −1.8 (3.4%) | 50.8 | 51.5 | 0.7 (3.3%) | Similar |
| Pulse rate | 76.5 | 83.8 | 7.3 (9.5%) | 72.3 | 76.3 | 4.0 (5.5%) | Group B was better |

Biomarkers measured at 41 days after the start of administration in this clinical test are shown in Table 12 below.

TABLE 12

|  | Group A (administered simultaneously; 8 patients) | | | Group B (administered at different times; 9 patients) | | | Results |
| --- | --- | --- | --- | --- | --- | --- | --- |
|  | Screening | D 42 | Change | Screening | D 42 | Change |  |
| AST (0-50 IU/L) | 25.4 | 27.4 | 2.0 (7.9%) | 26.1 | 28.0 | 1.9 (7.3%) | Similar |
| ALT (0-45 IU/L) | 40.4 | 41.4 | 1.0 (2.5%) | 37.1 | 34.7 | −2.44 (6.6%) | Group B was better |
| r-GTP (4-50) | 63.1 | 68.0 | +4.9 (7.8%) | 38.2 | 38.7 | +0.5 (1.3%) | Group B was better |
| CPK (51-246 IU/L) | 157.8 | 117.5 | −40.3 (25.5%) | 82.9 | 84.8 | 1.9 (2.3%) | Maintained in the normal range (A > B). |

From the clinical study results for the group administered simvastatin and losartan at different times and the group administered with the drugs simultaneously, it was proven that the group administered simvastatin and losartan at different times was excellent in all evaluation parameters including blood pressure reduction, lipid reduction and side effect-associated biomarkers. Especially, in the test group was no serious adverse events other than non-serious event, which generally occurred upon the simultaneous administration of each of simvastatin and losartan.

As a result, it was demonstrated through said clinical test that, when the angiotensin-II-receptor blocker and the HMG-CoA reductase inhibitor are administered at different times according to the present invention, the HMG-CoA reductase inhibitor shows a more excellent antihyperlipemial effect even at the same dose, when compared to simultaneous administration of single formulations of the angiotensin-II-receptor blocker and the HMG-CoA reductase inhibitor. In addition, the enhanced blood pressure-reducing effect of the angiotensin-II-receptor blocker, administered in order to reduce blood pressure was demonstrated, and it can be seen that the angiotensin-II-receptor blocker shows optimal effect due to the extension of the release time thereof.

Test Example 11

Clinical Study

A clinical study for evaluating drug interactions was carried out. Specifically, in order to examine the effects of drugs occurring when the drugs are absorbed at different time points, the differences in pharmacokinetic properties between administration of a combination preparation of Atorvastatin and Losartan according to the present invention, administration of single preparations of Atorvastatin or Losartan and co-administration of Atorvastatin and Losartan were examined.

This study is characterized as a crossover design study in which drugs were consecutively administered to four groups for 4 cycles. As shown in Table 13 below, test subjects were randomly divided into 4 groups. According to the groups and cycles shown in Table 13, a two-tablet combination of Example 32 (Atorvastatin (20 mg)/Losartan (50 mg)) and control drugs, one Lipitor tablet (40 mg), one Cozaar tablet (100 mg) and one Lipitor tablet (40 mg)+one Cozaar tablet (100 mg), were administered orally at 24-hr intervals for 5 consecutive days.

For the first 4 days of each cycle, each test subject was administered each test drug together with 240 mL of water at 8 a.m. every day before breakfast (fasted state). For drug administration on the last day (day 5) of each cycle, each subject fasted for 10 hours before drug administration and was administered orally each test drug together with 240 mL of water at 8 a.m. the next day.

At about 8 a.m. on the day of evaluating pharmacokinetics, a saline-locked angio-catheter was inserted into the vein of the arm or hand of each test subject, and 8 ml of blood was collected from each subject. During blood collection, about 1 mL of blood was discarded each time after collection in order to completely remove saline remaining in the blood collection set. Then, in the case of single administration of Atorvastatin or Losartan, 8 mL of blood was collected, and in the case of co-administration of Atorvastatin and Losartan, 12 mL of blood was collected. Also, in the case of administration of the drug combination and co-administration of the drugs, 2 mL of blood was collected for analysis of HMG-CoA reductase, and 5 mL of blood was collected for analysis of oxidative stress and safety biomarkers. Then, in order to prevent coagulation of blood remaining in the catheter, 1.5 mL of saline was injected into the catheter. Within 30 minutes after the collected blood, in a blood collection tube containing heparin, the blood was centrifuged at 3000 rpm for 10 minutes. After drug administration, the supernatant plasma was separated and stored at −70□ until analysis. In addition, for analysis of oxidative stress and safety biomarkers, 100 mL of urine was collected before drug administration on the first day of drug administration (before the last administration), and urine was collected for 6 hours after the last administration. A label for which study number, subject number, collection time (based on drug administration time), collection date, etc. was attached to each tube and fixed by tape before storage in a refrigerator.

TABLE 13

| Groups | Cycle 1 | Cycle 2 | Cycle 3 | Cycle 4 |
|---|---|---|---|---|
| Group 1 | ML | MA | M (Example 32) | M (A + L) |
| Group 2 | M (Example 32) | ML | M (A + L) | MA |
| Group 3 | M (A + L) | M (Example 32) | MA | ML |
| Group 4 | MA | M (A + L) | ML | M (Example 32) |

M (Example 32): two-tablet combination of Atorvastatin (20 mg)/Losartan (50 mg); administered once a day for 5 consecutive days
MA: one Lipitor tablet (40 mg; Pfizer Korea); administered once a day for 5 consecutive days
ML: one Cozaar tablet (100 mg; MSD Korea); administered once a day for 5 consecutive days
M(A + L): co-administration of one Lipitor tablet (40 mg; Pfizer Korea) and one Cozaar tablet (100 mg; MSD Korea); administered once a day for 5 consecutive days.
*: Drug-free interval: 17 days Pharmacokinetic data obtained from the above subjects are summarized in Table 14 below.

TABLE 14

|  | Atorvastoin | | Atorvastoin Metabolite | | Losartan | | Losartan Metabolite | |
|---|---|---|---|---|---|---|---|---|
|  | AUC (mg/mL · min) | Cmax (mg/mL) | AUC (mg/mL · min) | Cmax (mg/mL) | AUC (mg/mL · min) | Cmax (mg/mL) | AUC (mg/mL · min) | Cmax (mg/mL) |
| MA | 261.2 | 61.1 | 140.0 | 18.8 | — | — | — | — |
| ML | — | — | — | — | 894.0 | 504.9 | 5482.5 | 1107.5 |
| M (A + L) | 277.8 | 114.8 | 151.9 | 36.8 | 1038.3 | 857.0 | 5656.4 | 1447.9 |
| M (Example 32) | 229.5 | 68.8 | 141.4 | 30.0 | 861.8 | 502.9 | 5198.6 | 1282.6 |

As shown in Table 14 above, the maximum plasma concentration (Cmax) of Atorvastatin was 61.1 mg/mL in the case of single administration of Lipitor (MA) and 68.8 mg/mL in the case of administration of the delayed-release combination (M; Example 32), which were similar to each other, but was significantly increased to 114.8 mg/mL in the case of simple co-administration (M(A+L)) showing no delayed drug absorption. Also, the maximum plasma concentration of Losartan was 504.9 mg/mL in the case of single administration of Cozaar (ML) and 502.9 mg/mL in the case of administration of the delayed-release combination (M; Example 32), which were similar to each other, but was significantly increased to 857.0 mg/mL in the case of simple co-administration (M(A+L)) showing no delayed drug absorption. In this study, when the delayed-release combination (core tablet of Example 32) was administered, no Losartan was detected in the subject's blood until 1.5 hours after administration, suggesting that the absorption of Losartan is delayed for 1.5 hours or more.

Specifically, as can be seen from the above study results, in the case in which Atorvastatin is first absorbed into the subject and then Losartan is absorbed after a delay time of 1.5 hours or more, drug interactions mediated by P-glycoprotein transporters and cytochrome P450 metabolic enzymes are avoided. Thus, administration of the delayed-release combination of Atorvastatin and Losartan shows pharmacokinetic properties comparable to the single administration of each of the drugs, and the pharmacokinetic properties thereof are significantly different from those of co-administration of the two drugs. This suggests that administration of the delayed-release combination of Atorvastatin and Losartan can reduce the possibility of an occurrence of side effects, such as an excessive increase in the maximum blood concentration of Atorvastatin, and rhabdomyolysis that can arise therefrom.

The invention claimed is:

1. A method of preventing or treating hypertension, hyperlipidemia, cardiovascular diseases, cardiopulmonary diseases, pulmonary diseases, renal disorders, or metabolic syndromes, which comprises administrating to a subject a therapeutically effective amount of an angiotensin-II-receptor blocker and an HMG-CoA reductase inhibitor, wherein the angiotensin-II-receptor blocker is absorbed substantially later than the HMG-CoA reductase inhibitor.

2. The method of claim 1, wherein the administration is performed such that the angiotensin-II-receptor blocker is absorbed 1.5-6 hours substantially later than the HMG-CoA reductase inhibitor.

3. The method of claim 1, wherein the angiotensin-II-receptor blocker and the HMG-CoA reductase inhibitor are administrated in the form of a combination preparation.

4. The method of claim 3, wherein the combination preparation is designed so that release of angiotensin-II-receptor blocker is delayed substantially later than the HMG-CoA reductase inhibitor, thereby angiotensin-II-receptor blocker is absorbed 1.5-6 hours substantially later than the HMG-CoA reductase inhibitor.

5. The method of claim 4, wherein the angiotensin-II-receptor blocker is lag time delayed released such that a dissolution rate of the angiotensin-II-receptor blocker is less than 10% up to a total of 120 minutes, and less than 20% up to a total of 240 minutes.

6. The method of claim 4, wherein the combination preparation is administrated between 5 p.m, and 10 p.m, once a day.

7. The method of claim 1, wherein the angiotensin-II-receptor blocker and the HMG-CoA reductase inhibitor are administrated in the form of single preparations.

8. The method of claim 1, wherein the angiotensin-II-receptor blocker is administrated 1.5-6 hours later than the HMG-CoA reductase inhibitor.

9. The method of claim 1, wherein the angiotensin-II-receptor blocker is one or more components selected from the group consisting of losartan, valsartan, irbesartan, candesartan, telmisartan, eprosartan, olmesartan and pharmaceutically acceptable salts thereof.

10. The method of claim 1, wherein the HMG-CoA reductase inhibitor is one or more components selected from the group consisting of simvastatin, lovastatin, atorvastatin, pitavastatin, rosuvastatin, fluvastatin, pravastatin and pharmaceutically acceptable salts thereof.

* * * * *